(12) United States Patent
Olsen et al.

(10) Patent No.: US 7,991,593 B2
(45) Date of Patent: Aug. 2, 2011

(54) OPTIMISATION OF SEQUENTIAL COMBINATORIAL PROCESS

(75) Inventors: Tor-Morten Överby Olsen, Frändefors (SE); Karl Henrik Runnemalm, Vänersborg (SE); Andrew John Keane, Hampshire (GB); Ivan Voutchkov, Hampshire (GB); Atul Bhaskar, Hampshire (GB)

(73) Assignees: Volvo Aero Corporation, Trollhattan (SE); University of Southampton, Hampshire (GB)

( * ) Notice: Subject to any disclaimer, the term of this patent is extended or adjusted under 35 U.S.C. 154(b) by 1156 days.

(21) Appl. No.: 10/571,343

(22) PCT Filed: Sep. 10, 2004

(86) PCT No.: PCT/GB2004/003877
§ 371 (c)(1),
(2), (4) Date: Mar. 10, 2006

(87) PCT Pub. No.: WO2005/027002
PCT Pub. Date: Mar. 24, 2005

(65) Prior Publication Data
US 2007/0043622 A1    Feb. 22, 2007

(30) Foreign Application Priority Data

Sep. 12, 2003 (GB) .................................. 0321420.2
Sep. 12, 2003 (GB) .................................. 0321427.7
Sep. 12, 2003 (SE) ...................................... 0302474

(51) Int. Cl.
*G06F 7/60* (2006.01)
*G06F 15/18* (2006.01)
(52) U.S. Cl. ............................................. 703/2; 706/13
(58) Field of Classification Search .................. 706/13; 703/2; 700/100–102; 705/8, 9
See application file for complete search history.

(56) References Cited

U.S. PATENT DOCUMENTS

| 5,229,948 | A  | * | 7/1993 | Wei et al. ........................ 700/99 |
| 6,349,467 | B1 |   | 2/2002 | Karafillis et al. |
| 7,047,169 | B2 | * | 5/2006 | Pelikan et al. .................... 703/2 |
| 7,082,338 | B1 | * | 7/2006 | Chen et al. ...................... 700/31 |
| 2004/0030428 | A1 | * | 2/2004 | Crampton et al. ............ 700/101 |

FOREIGN PATENT DOCUMENTS

WO    01/30532    5/2001

OTHER PUBLICATIONS

Kadivar, M.H. et al. "Optimizing welding sequence with genetic algorithm." *Computer Mechanics*. 26 (2000): 514-519.
Voutchkov, Ivan et al. "Combinatorial optimization of welding sequences." *Online*. http://web.archive.org/web/20030804223 (Aug. 2003):1-2.

\* cited by examiner

*Primary Examiner* — Paul L Rodriguez
*Assistant Examiner* — Juan Ochoa
(74) *Attorney, Agent, or Firm* — Renner, Otto, Boisselle & Sklar, LLP

(57) ABSTRACT

A method of optimising a sequential combinatorial process comprising an interchangeable sequence of events uses a master model to model a selection of the possible sequences. Information derived from the master model is used in a surrogate model that approximates the master model. The surrogate model calculates all possible sequences using an algorithm to select information calculated by the master model that most closely matches the events of a present sequence, following a prioritised system so that the best match is used wherever possible. All results from the surrogate model are compared to identify the modelled sequence that gives results closest to a desired optimum result.

64 Claims, 8 Drawing Sheets

| Sequence number | Welding position | | | | | |
| --- | --- | --- | --- | --- | --- | --- |
| | 1 | 2 | 3 | 4 | 5 | 6 |
| 1 | 1 | 2 | 3 | 4 | 5 | 6 |
| 2 | -1 | -2 | -3 | -4 | -5 | -6 |
| 3 | -2 | -4 | -6 | 1 | 3 | 5 |
| 4 | -3 | 5 | 4 | -2 | -6 | -1 |
| 5 | 4 | 3 | 1 | -6 | -2 | -5 |
| 6 | -6 | 5 | 3 | -1 | 4 | 2 |
| 7 | -6 | -1 | -5 | -2 | -4 | 3 |
| 8 | 6 | 5 | -1 | -4 | 2 | -3 |
| 9 | -1 | 6 | 4 | -3 | 5 | -2 |
| 10 | -5 | -4 | -3 | -6 | 2 | -1 |
| 11 | -4 | -2 | -1 | -6 | -5 | -3 |
| 12 | 2 | -6 | -4 | -1 | -3 | -5 |
| 13 | 3 | -6 | 4 | -5 | -1 | 2 |
| 14 | 5 | -6 | -3 | -2 | 1 | -4 |
| 15 | -5 | 1 | -3 | 2 | -4 | 6 |
| 16 | -4 | 1 | -5 | 2 | 6 | -3 |
| 17 | -3 | -1 | 5 | 2 | 4 | -6 |
| 18 | -2 | 3 | -5 | 4 | 1 | 6 |
| 19 | 1 | -2 | 4 | 6 | -5 | 3 |
| 20 | 2 | -5 | 6 | -1 | 3 | -4 |
| 21 | 3 | -2 | 6 | -4 | 5 | 1 |
| 22 | 5 | -3 | 6 | 2 | 1 | 4 |
| 23 | -6 | 3 | 2 | 5 | -4 | 1 |
| 24 | 6 | 1 | 5 | -3 | 4 | 2 |
| 25 | 6 | -2 | -3 | 1 | 5 | 2 |
| 26 | 3 | 6 | -5 | 2 | 1 | 4 |
| 27 | 4 | -1 | -2 | 5 | 6 | 3 |

Fig. 9

| 0 | -0.04637 | 0.015221 | -0.17027 | -0.04628 | -0.00126 | -0.02497 | -0.05008 | -0.15566 | 0.042639 | -0.05222 | 0 |
|---|---|---|---|---|---|---|---|---|---|---|---|
| -0.12721 | 0 | 0.109013 | -0.07953 | 0.046241 | 0.025011 | 0.067492 | -0.00346 | -0.12583 | 0.038388 | 0 | -0.12707 |
| -0.00466 | 0.017682 | 0 | 0.016915 | 0.073715 | 0.112701 | 0.085963 | 0.032824 | -0.03344 | 0 | 0.056775 | -0.14728 |
| -0.12857 | 0.028058 | 0.072054 | 0 | -0.01247 | 0.050471 | 0.015521 | -0.01708 | 0 | 0.053021 | -0.01724 | -0.17656 |
| -0.13223 | -0.03817 | 0.116399 | -0.09991 | 0 | 0.066386 | 0.001524 | 0 | -0.18364 | 0.070376 | 0.019423 | -0.21464 |
| -0.09322 | 0.047027 | 0.153193 | -0.07155 | 0.02736 | 0 | 0 | -0.00611 | -0.03574 | 0.118441 | 0.075124 | -0.08085 |
| -0.18349 | 0.002075 | 0.126048 | -0.12823 | 0.004494 | 0.076159 | 0.025243 | -0.04623 | -0.15617 | 0.094755 | -0.00836 | -0.18761 |
| -0.21617 | -0.03299 | 0.11585 | -0.08414 | 0.009471 | 0 | 0 | -0.05895 | -0.11923 | 0.023736 | 0.009762 | -0.19148 |
| -0.24327 | -0.06272 | 0.059065 | -0.04695 | 0 | 0.009273 | -0.00861 | 0 | -0.1709 | 0.068548 | -0.05928 | -0.19599 |
| -0.26951 | -0.12489 | 0.119385 | 0 | -0.0362 | 0.051475 | -0.07095 | -0.00645 | 0 | -0.01016 | 0.005272 | -0.26855 |
| -0.10497 | 0.015377 | 0 | -0.06404 | 0.050261 | 0.05539 | 0.020241 | 0.019658 | -0.1848 | 0 | -0.01315 | -0.11685 |
| -0.20513 | 0 | 0.063895 | -0.16149 | 0.007902 | 0.025045 | 0.016983 | 0.000537 | -0.12 | 0.013857 | 0 | -0.16623 |
| 0 | -0.10854 | 0.002057 | -0.17873 | -0.11519 | -0.07091 | -0.07587 | -0.10017 | -0.21961 | -0.01131 | -0.11318 | 0 |

Fig. 11

OPTIMISATION OF SEQUENTIAL COMBINATORIAL PROCESS

This application is a national phase of International Application No. PCT/GB2004/003877 filed Sep. 10, 2004 and published in the English language.

BACKGROUND OF THE INVENTION

The present invention relates to the optimisation of sequential combinatorial processes.

There are numerous examples of processes that comprise the performance of a to series of steps, the end result of which can be optimised by carrying out the steps in a preferred manner. Manufacturing processes, for example, may include steps in which the size, quantity, duration, pressure, temperature, viscosity, etc, of particular variables affects the quality of the manufactured product. Industry is naturally concerned with achieving quality, so it is frequently desirable to optimise the various steps to obtain the best possible end result.

This optimisation is often done by modelling of the process. In this way, different values of a parameter or group of parameters can be compared to determine which gives the best result. One modelling technique that is of particular interest due its high accuracy and ability to cope with complex scenarios is finite element (FE) analysis. For the type of process in question, the model generally considers the parameters of interest as being defined in a continuous numerical space in which the parameters may take any value, and seeks the optimum value of each having regard to the others. However, in terms of computational time required, this is an expensive approach. A single "run" of an FE model for one set of values of the parameters may take many hours, and typically there are many different values to be considered. This means that the model may take many thousands of iterations to converge to any optimum solution, so that a full study of the process may take an unfeasibly long time. The cost of this may outweigh any benefit achieved from optimising the process.

This disadvantage has been addressed by so-called surrogate modelling. The idea of using surrogate models in optimisation has been widely explored for problems related to expensive computations. The surrogate is a simple approximation of the FE (or other complex) model, with a shorter iteration time so that it is faster to compute. A well-known surrogate model is kriging, but any other approximation method suitable to the specific problem can be used. Results from a few runs of the finite element analysis model are supplied to the surrogate model, to "train" it. The quantity of these runs depends on the complexity of the process under study; usually 20-30 runs are enough to give a sufficient level of accuracy. Once the surrogate is trained, it is put through an optimisation cycle, in which it calculates the result of the process for all possible values of the parameter or parameters of interest, and returns the value corresponding to the optimal result of the process. However, this optimal value is based on the approximation of the surrogate model and may be inaccurate. Therefore, it is common to run the FE model for the same values of the parameters, and compare the result with that from the surrogate. If there is a significant difference, the result of this latest FE run is then fed to the surrogate to improve its training, and the surrogate is again put through an optimisation cycle, and so on until acceptable agreement between the two models is reached. In this way, the surrogate model becomes more accurate in the region of the optimum, because accuracy is only added where and when it is needed. The overall computational time needed to obtain the optimal value is reduced by transferring the bulk of the computational load from the slow FE model to the faster surrogate. For example, a single FE run can take about 48 hours, while 50000 surrogate evaluations can be performed in less than ten minutes.

Further, the accuracy can be enhanced by careful selection of the initial FE model runs to include a range of parameter values that covers those thought likely to be of importance in determining the optimal value. This is known as Design of Experiments (DoE), and a voids potential waste of computational time in modelling scenarios that lie far from the desired result. An example of a modelling process that uses finite element analysis together with DoE can be found in U.S. Pat. No. 6,349,467 [1], where the technique is applied to optimising the steps in a process for manufacturing deflector plates for gas turbine engine combustors so as to avoid undesirable intermediate heat treatment of sheet metal used to form the deflector plates.

To date, surrogate-supplemented FE modelling has been applied to a wide range of problems in which it is desired to optimise the numerical value of one or more parameters used in a process. The problems have been limited to those which can be approximated by a surrogate model function that depends on variables that have a continuous or discrete nature and can be physically or quantitatively expressed. However, there is a further set of processes which can benefit from optimisation, but to which the known surrogate modelling techniques cannot be applied, because the problem does not lie in finding an optimum numerical value of a parameter. These processes are those that comprise several steps, or events, that can be performed, or combined, in any order, or sequence, to achieve the end result of the process. However, the quality of the end result depends on the order in which the steps are performed. In other words, there are no surrogate model optimisation techniques available in the combinatorial domain, in which variables have no physical meaning. The goal is to determine the optimum ordering of the events, so as to get the best result. Hence, this problem can be referred to as a sequential combinatorial optimisation problem; in what sequence should the events be combined to give the optimum result? It will be appreciated that this is a problem distinct from that of determining the optimum value of a quantifiable parameter; individual events and their ordering are non-numerical items without physical meaning. Thus far, it has been largely necessary to rely on full FE analysis studies to solve these kinds of optimisation problems.

Great benefit would be conferred by a method offering an improved optimisation technique for sequential combinatorial processes.

SUMMARY OF THE INVENTION

Accordingly, a first aspect of the present invention is directed to a method of optimising a sequential combinatorial process comprising a plurality of interchangeable events performable in any of many sequences to achieve an end result of the process, the end result being defined by an operation parameter, the method comprising: using a design of experiments comprising a plurality of sequences selected from the many sequences, each sequence from the design of experiments being linked to information regarding values of contributions to the end result, in terms of the operation parameter, for each event in each sequence; using a surrogate model of the process that takes as an input a sequence of the events and determines a value of the end result by summing values of contributions to the end result for each event in the input sequence, where the values of the contributions are selected from the values of the contributions from the operation parameter information according to an algorithm that searches the design of experiments for a match between each event of the input sequence and the events in the sequences of the design of experiments according to a priority list of matching conditions and retrieves the value of the contribution for the matched event; running a plurality of the many sequences through the surrogate model and recording the value of the end result for each sequence; and identifying an optimum sequence by searching the recorded values of the end result from the surrogate model to find a recorded optimum value of the operation parameter, the sequence that gives this recorded optimum value being the optimum sequence.

The invention thus applies a surrogate model to the optimisation of sequential combinatorial problems, such as can otherwise only be solved by complex modelling such as finite element analysis modelling. It proposes a fast and efficient solution to the problem of the very time-consuming nature of complex modelling, in part because it is able to extract useful information from that available by accessing the information according to a priority list based on its usefulness. This allows more accurate information to be utilised in preference to less accurate information wherever possible, so that the final result produced quickly by the surrogate model is a good approximation to more accurate results that may be obtainable more slowly from conventional complex models.

Thus there is a great reduction in computational expense, which has been found to be without significant loss of accuracy. The design of experiments can be implemented in a flexible manner so that the method can be adapted for increasing volumes of information, allowing for dynamic expansion as more data is made available, which increases the accuracy.

The method has been practically applied to real engineering situations, and has amply demonstrated its benefits by optimising a welding process using only twenty-seven runs of a finite element analysis master model, out of a possible 46080 combinations.

In some embodiments, the method may further comprise obtaining the information to which each sequence from the design of experiments is linked by running each sequence from the design of experiments through a master model of the process that takes as an input a sequence of the events and determines a value of the end result and values of contributions to the end result of each event in the input sequence. Using a master model in this way provides the information necessary for the surrogate model in an accurate manner without any need for practical implementation of the process. However, the overall optimisation can still be very much faster than optimisation using the master model alone, because the prioritised matching procedure allows the best use to be made of a small amount of information. Thus, sufficiently accurate results can be achieved using just a small number runs of the complex, master model, instead of the highly time-consuming full set of runs that would be needed if the master model alone were relied upon. A large proportion of the computational burden can be transferred to the surrogate model, speeding the optimisation considerably.

In this context, the method may further comprise constructing the master model before running each sequence from the design of experiments through the said master model. Thus, a master model specifically tailored to the procedure of interest can be made and used, which will enhance accuracy.

Preferably, the surrogate model is a simplified approximation of the master model. The transfer of the computational burden from the master to the surrogate model is best exploited if the surrogate model is as simple as accuracy will allow, since a simple model can typically be calculated more quickly.

The method may further comprise, after identifying the optimum sequence, running the identified optimum sequence through the master model to determine a value of the end result, and comparing the recorded optimum value for the identified optimum sequence determined by the surrogate model with the end result determined by the master model to check accuracy of the identification of the optimum sequence. Since the master model is more accurate than the surrogate model, if time permits it is valuable to run the identified optimum sequence through the master model so see if the two models agree. Agreement is a good indicator that the identified sequence really is optimal. It can then be applied to the process with a high degree of confidence. Moreover, if an unacceptable discrepancy is found between the two results, the additional run through the master model has not been wasted, since additional accurate information is now available and can be added to the design of experiments to improve the accuracy of future runs of the surrogate model. Therefore, the method may usefully further comprise, if the recorded optimum value for the identified optimum sequence determined by the surrogate model and the end result determined by the master model are found to differ by an amount unacceptable for the process, adding the identified optimum sequence to the design of experiments so that this sequence and values of contributions to the end result for each event as determined by the running of the identified optimum sequence through the master model are available for searching and retrieval by the surrogate model algorithm; running a plurality of the many sequences through the surrogate model to determine new values of the end result for each sequence; and identifying a new optimum sequence from the new end results.

Additionally; the method may further comprise repeating the steps of the preceding paragraph for the new identified optimum sequence until the recorded optimum value for the identified optimum sequence determined by the surrogate model and the end result determined by the master model differ by an amount acceptable for the process. This looping behaviour allows the surrogate model to converge to an accurate result by providing it with increasing amounts of accurate information from the master model which are known to be biased towards optimum performance for the process, since they have been identified by the surrogate model. Thus, the looping is efficient as well as accuracy-enhancing.

In alternative embodiments, method may further comprise obtaining the information to which each sequence from the design of experiments is linked by performing the sequential combinatorial process using each of the sequences in the design of experiments, and recording the values of contributions to the end result for each event in each sequence. This approach, in which real experimental data is used to provide the information used by the surrogate model, may be preferred over more abstract approaches in certain circumstances. For example, for a simple process it may be quicker and/or less expensive to perform the process several times for different sequences than to construct a complex master model, or to otherwise obtain the information by calculation. Accuracy will be better than other techniques such as adaptation of data obtained from or calculated for a related process. The accuracy of this embodiment will depend in part on the accuracy of the experimental measurements, and how easy it is to determine the contributions of the various events to the end result.

The method may additionally comprise constructing the surrogate model before running the plurality of the many sequences through the said surrogate model. A surrogate model closely matched to a particular process can be constructed, with a degree of simplicity appropriate to the accuracy required from and the time available for optimisation of the process.

In some embodiments, the priority list may comprise a hierarchy of matching conditions requiring a decreasing level of matching between an event in the sequence input to the surrogate model and events in the sequences of the design of experiments in terms of position of the event within the input sequence and/or events preceding the event in the input sequence. This makes efficient use of the available information regarding the contributions of the various events, since the most accurate calculations or measurements of the contributions (which correspond to the best matches in the sequences) are used whenever possible, and replaced by the nearest match only where necessary.

To assist in achieving a good match in the events, the matching conditions may be defined so as to have: an order that specifies a number of events preceding an event in the sequence input to the surrogate model that are required to be matched with events preceding an event in the sequences of the design of experiments; and a type that specifies whether or not a position of an event in the sequence input to the surrogate model within that sequence matches a position of an event within the sequences of the design of experiments, such that a type 1 match requires that the position of an event in the input sequence matches the position of an event within the sequences of the design of experiments, and a type 2 match does not require that the position of an event in the input sequence matches the position of an event within the sequences of the design of experiments.

For example, in the case of a sequence comprising n events, the priority list may comprise the following matching conditions:

a match of order n of type 1;
a match of order n of type 2;
a match of order n−1 of type 1;
a match of order n−1 of type 2
a match of order 1 of type 1;
a match of order 1 of type 2;
a match of an event at any position in the sequence with the same event occurring in a first position of any sequence in the design of experiments.

This gives higher priority to matching of the preceding events, by looking for the same sub-sequence of events as in the sequence being modelled regardless of position, before moving on to search for a truncated sub-sequence. For some applications, however, it may be found or suspected that absolute position is more important then the effect of preceding events, so that alternatively, for a sequence comprising n events, the priority list may comprise the following matching conditions:

a match of order n of type 1;
a match of order n−1 of type 1;
a match of order of n−2 of type 1;
. . .
a match of order 1 of type 1;
a match of order n of type 2;
a match of order n−1 of type 2;
a match of order n−2 of type 2;
. . .
a match of order 1 of type 2;

a match of an event at any position in the sequence with the same event occurring in a first position of any sequence in the design of experiments.

Advantageously, the design of experiments may comprise a selection of sequences from the many sequences that contain events which provide matches with at least all combinations of events of a selected order and type of matching condition. This ensures that the operation parameter information is focussed on where it will be of most value, with the aim of providing an accurate result with the smallest amount of information. For various embodiments, this approach means that only the smallest number of master model runs or performances of the process need be performed, thus simplifying and speeding the optimisation. However, the extra consideration required in determining which sequences are needed for this may be deemed not to be worthwhile. In that case, as an example, the design of experiments may alternatively comprise a random selection of sequences from the many sequences. In any case, regardless of the type of design of experiments, the method may further comprise determining the design of experiments. This allows an appropriate design of experiments for any particular process to be used, which potentially gives better accuracy than using a previous or standard design known to be reasonably suitable for the process, for example.

Running a plurality of the many sequences through the surrogate model may comprise running all of the many sequences through the surrogate model. This naturally takes a little longer than running a subset of the sequences, but should give the most accurate result, although in a many cases a satisfactorily accurate result will be readily obtainable from a subset. The extra calculation time can be balanced against the improved accuracy when deciding how many sequences to run through the surrogate model.

The probable substantial calculation required, especially in the case of a complex master model, suggests that in a preferred embodiment, the method is implemented at least in part by computer. This serves to take good advantage of the substantial decrease in optimisation time offered by the present invention.

Once the optimum sequence has been identified, it can be applied to the process of interest. Therefore, the method may further comprise carrying out the sequential combinatorial process using the identified optimum sequence of events.

As an example application of the invention, the sequential combinatorial process may comprise welding a vane to a ring of a gas turbine tail bearing housing, the events being individual welding paths arranged in a sequence, the operation parameter defining the end result being a distortion of a tip portion of the vane, and the optimum value of the operation parameter being a minimum value of the distortion.

A second aspect of the present invention is directed to a computer program product comprising machine-readable instructions for implementing a method of optimising a sequential combinatorial process comprising a plurality of interchangeable events performable in any of many sequences to achieve an end result of the process, the end result being defined by an operation parameter, the instructions operable to instruct a machine to: store a design of experiments comprising a plurality of sequences selected from the many sequences; store information linked to each sequence from the design of experiments, the information regarding values of contributions to the end result, in terms of the operation parameter, of each event in each sequence from the design of experiments; run a plurality of the many sequences through a surrogate model of the process that takes as an input a sequence of the events and determines a value of the end result by summing values of contributions to the end result for each event in the input sequence, where the values of the contributions are selected from the values of the contributions from the operation parameter information according to an algorithm that searches the design of experiments for a match between each event of the input sequence and the events in the sequences of the design of experiments according to a priority list of matching conditions and retrieves the value of the contribution for the matched event, and record the value of the end result for each sequence; and identify an optimum sequence by searching the recorded values of the end result from the surrogate model to find a recorded optimum value of the operation parameter, the sequence that gives this recorded optimum value being the optimum sequence.

A computer program product for implementing the invention can be in the form of a computer program on a carrier medium. The carrier medium could be a storage medium, such as a solid state, magnetic, optical, magneto-optical or other storage medium. Alternatively, the carrier medium could be a transmission medium such as broadcast, telephonic, computer network, wired, wireless, electrical, electromagnetic, optical or indeed any other transmission medium.

A third aspect of the present invention is directed to a computer system for implementing a method of optimising a sequential combinatorial process comprising a plurality of interchangeable events performable in any of many sequences to achieve an end result of the process, the end result being defined by an operation parameter, the computer system comprising: memory for storing a design of experiments comprising a plurality of sequences selected from the many sequences, and information linked to each sequence from the design of experiments, the information regarding values of contributions to the end result, in terms of the operation parameter, of each event in each sequence from the design of experiments; and a processor operable to: run a plurality of the many sequences through a surrogate model of the process that takes as an input a sequence of the events and determines a value of the end result by summing values of contributions to the end result for each event in the input sequence, where the values of the contributions are selected from the values of the contributions from the operation parameter information according to an algorithm that searches the design of experiments for a match between each event of the input sequence and the events in the sequences of the design of experiments according to a priority list of matching conditions and retrieves the value of the contribution for the matched event, and record the value of the end result for each sequence in the memory; and identify an optimum sequence by searching the recorded values of the end result from the surrogate model to find a recorded optimum value of the operation parameter, the sequence that gives this recorded optimum value being the optimum sequence.

Other aspects, embodiments and examples of the present invention are set out in the appended claims.

BRIEF DESCRIPTION OF THE DRAWINGS

For a better understanding of the invention and to show how the same may be carried into effect reference is now made by way of example to the accompanying drawings in which:

FIG. 9 shows a table of sequences used in a design of experiments for optimising the welding process according to an embodiment of the present invention;

FIG. 11 shows a matrix of the displacement of a part of the vane caused by each occurrence given in FIG. 10;

DETAILED DESCRIPTION

Figure 1:
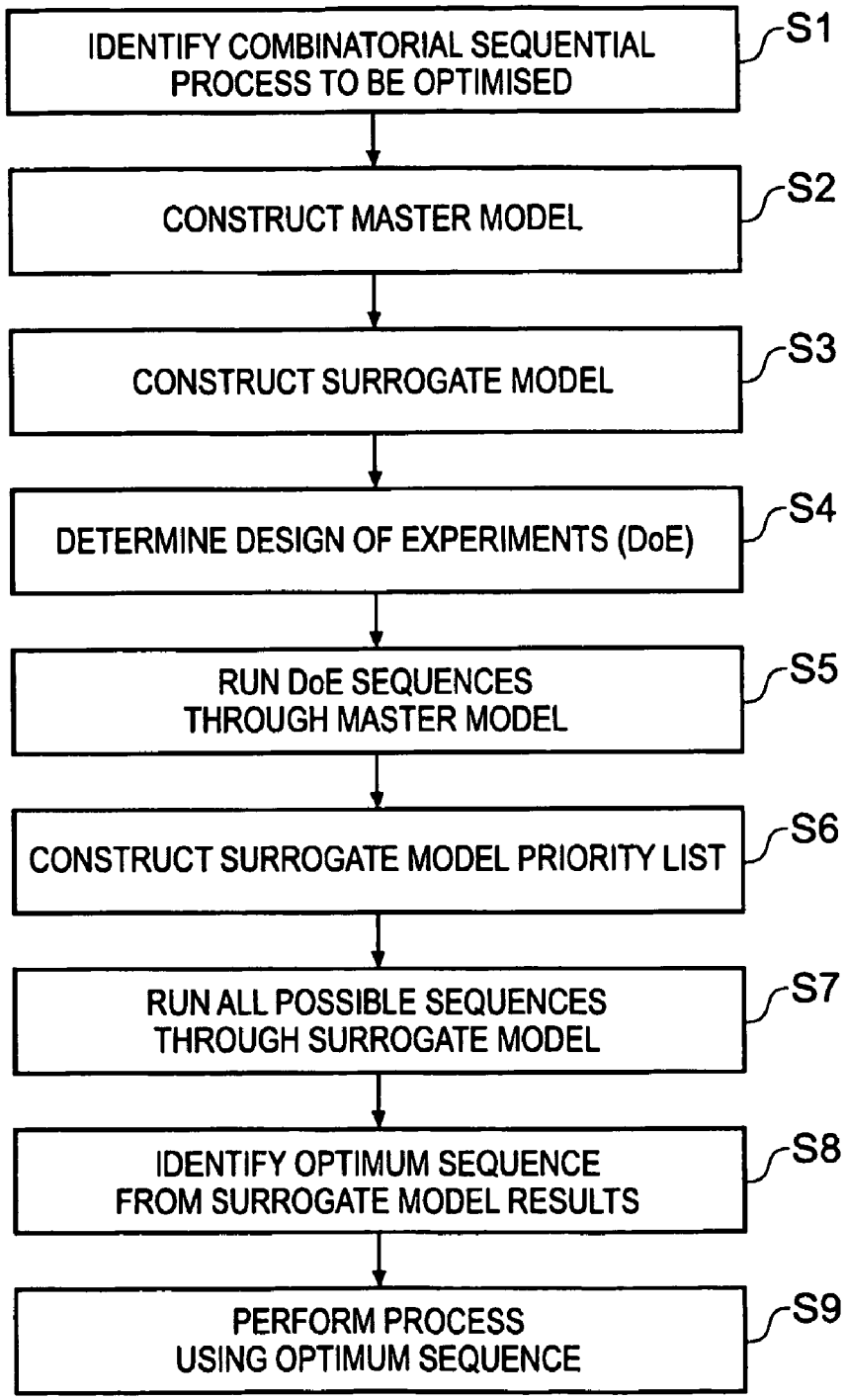
FIG. 1 shows a flow chart of steps in an embodiment of a method according to the present invention.

The present invention proposes a technique for applying a surrogate model approach, such as has previously been used for finding optimal solutions to continuous numerical problems, to sequential combinatorial problems. The surrogate model drastically reduces the computational expense required to optimise such processes compared to conventional approaches that rely on complex computer modelling methods such as finite element analysis.

A sequential combinatorial process is a process comprising a plurality of steps, or events, which are interchangeable in that they can be performed in any of several or many sequences, perhaps with some events replacing others or with a choice of ways of performing each event, to give the same general end result, but in which the quality of that end result depends on the particular sequential order of the events.

Therefore, for each position in the sequence, an event is performed, where the event may be selected either from a group of events equal to the number of positions in the sequence, or from a larger pool of events. In the latter case, the larger pool may result from some events being able to be left out of the process or replaced by other events, or alternatively by some or all of the events having associated parameters that can take different values (performing a particular step at one of several different temperatures or for one of several durations, for example) so that each event has several possible configurations that can each be considered as an event in its own right although only one of the configurations will be included in any given sequence.

The end result may be considered to be defined by an operation parameter. The nature of the operation parameter will depend on the particular process, it may be, for example, the dimension of part of a component manufactured by the process, or the time taken for the process to be performed.

Thus, for each possible sequence of the process, there is an end result that has a value defined in terms of the operation parameter.

In the dimension example above, the end results will be different magnitudes of the dimension.

In the time example above, the end results will be different amounts of time.

Each event in a given sequence contributes to the end result in some way that will depend both on its position in the sequence and also on the nature of the event itself, so that modifying the events selected will change the value of the end result.

From a range of sequences, there will be a sequence with an end result the value of which gives an optimum value of the operation parameter, such as the quickest time or the smallest dimension. It is not always obvious which sequence gives this optimal result, so it is desirable to be able to determine that sequence, which can be thought of as optimisation of the combinatorial process. To date, this has generally only been achievable using complex modelling. Typically, such as in the case of finite element (FE) analysis models, it can take many hours for a single sequence to be modelled. For a process with even a relatively modest number of events, the total number of combinations of events can be enormous, so that to check every combination with the model becomes unfeasible. The present invention proposes the use of a simpler surrogate model to take some of the computational burden, and hence speed up the process.

The present invention thus provides a technique for combinatorial optimisation. The optimisation is the process of finding one or more best or optimal solutions in a well-defined discrete problem space. The space is discrete since there are only a finite number of events, and each event is either in or not in a given sequence; thus the combinatorial sequential problem is concerned with the efficient allocation of limited resources to meet desired objectives when the values of some or all variables are restricted to be integral. Constraints on basic resources, such as time, labour, supplies or capital may restrict the possible alternatives that are considered feasible. Such problems occur in almost all fields of management such as finance, marketing, production, scheduling, inventory control, facility location and layout, database management, and also in many engineering disciplines. Examples are the optimal design of waterways or bridges, VLSI circuitry design and testing, the layout of circuits to minimise the area dedicated to wires, design and analysis of data networks, solid-waste management, determination of ground states of spin-glasses, determination of minimum energy states for alloy construction or alloy separation, energy resource-planning models, logistics of electrical power generation and transport, scheduling of goods in work-through manufacturing facilities, and problems in crystallography. All of these processes can benefit from application of the optimisation technique proposed herein.

In fact, the present invention is applicable to any sequential process in which the ordering of events in a sequence affects the outcome of the process. The examples of applications given above demonstrate the very wide applicability of the invention. In addition to these examples, some processes which the invention can be used to optimise include the following:

a. Machining a component from a workpiece. The events comprise various cutting steps to form the different parts of the component, and it is desired to find the sequence which best achieves the desired shape and/or quality of the component. This may be defined in terms of surface finish, grain orientation, and/or depth of surface material that is plastically deformed by the cutting tool, for example. These desired features comprise the operation parameter described above. An application of this type includes cutting material away from the workpiece in such a sequence that the component obtains or preserves a desired structural stiffness during machining so that minimum flutter or vibrations occur during machining. In this case, the operation parameter is the flutter, and its optimum value is the minimum amount.

b. Heat treatment of a component. This involves the way in which a furnace used for the heat treatment is operated, so that possible events include the position and operation of fan outlets, position and operation of guidance for hot or cold air flow, altering or not altering of the airflow during any stage of the heat treatment, holding times and cooling times. The object is to achieve an end result of a desired shape, stiffness or material microstructure of the component, for example; one or more of these will therefore be the operation parameter, with the desired shape, etc. being the optimum value.

c. Shaping and/or forming a component. Such a process is a sequence of steps for shaping and forming of different parts of a workpiece (the events), with the aim of achieving a desired shape, structural stiffness or material microstructure (the end result). An alternative end result is how the state of the manufactured workpiece resulting from a given sequence affects a further component of which the workpiece is intended to form a part.

d. A manufacturing sequence comprising a combination of the above fabrication processes, where the various processes become the events that can be performed in various orders and in different manners to affect the quality of the end product. For example, it might be desired to determine where in a manufacturing sequence one or more heat treatments should be applied in order to achieve a desired shape, structural stiffness or material microstructure of a produce, taking into account that certain mechanical and/or material characteristics are imparted to the product by processes such as mining, casting, machining, forming and welding.

e. Flow of material and/or components. In a manufacturing process, material and components used in the process will typically need to be moved through a factory or plant, and the sequence of steps used to achieve the flow will affect parameters such as the duration and output rate of the process. This may include the overall flow through a whole factory or even between factories. The steps or events may include, for example, transportation of an item between different machines and storage and processing sites. This may extend to determining optimum positions of machines on a factory floor, since the contribution of each transportation event to the overall flow will depend on the position of the machines involved, so a large pool of events is available, corresponding to the various possibilities for positioning the machines.

f. Pumping of gas or oil through a pipeline network. The pattern of delivery of the gas or oil to customers, for example, can be affected by different network component designs and operating parameters such as the opening and closing of valves and the pumping rate; events corresponding to individual portions of the network with different configurations can be sequenced together to determine the best arrangement for optimal delivery. The combinatorial aspects of this problem can be further combined with stochastic and nonlinear effects if desired; this may improve accuracy of the optimisation process by allowing extra detail to be taken into account in the various events.

g. Chemical and material science applications, such as determining the optimum sequence for adding different ingredients or constituents to achieve a desired mixture. Possible events may thus include the various ingredients in different proportions, at different temperatures or concentrations, and with different mixing techniques, which are then arranged in a sequence to achieve the overall mixture. The quality of the mixture is the end result of the process, defined by operation parameters such as stability, purity or homogeneity. This also includes optimisation of energy states for alloy construction or alloy separation.

h. Computational biology. In this field, various problems are typically analysed with numerical methods describing the behaviour of biological components such as molecules, proteins and genomes. The present invention may be adopted to reduce the computational effort of exploring the large volume of possible combinations of subsequent reactions taking place during, for instance, the creation of new molecules and the replication processes in DNA structures. Numerical methods of this type include directed and undirected graphs, Byesian networks, Boolean networks, generalised logical networks, nonlinear ordinary differential equations, piecewise-linear differential equations, qualitative differential equations, partial differential equations and other special distributed models, stochastic master equations and rule-based formalism. A particular example where the present invention is expected to be of particular benefit is in the modelling and simulation of genetic regulatory systems where an analysis of the interaction between DNA, RNA, proteins and small molecules is required. The interaction involves several steps which may occur in various sequences; these can be studied using the present invention to determine how a particular end result of an interaction comes about, for example. If the end result is known, this represents the optimum value, so that the sequence which gives that value can be identified.

i. Fleet management. It is desirable for cargo transportation and logistics providers using fleets of buses, trucks, airliners, tankers, cars, military vehicles, etc. to deliver or collect goods or people to or from a variety of locations to be able to optimise their schedules to maximise utilisation of available resources. A particular example is a cargo company optimising the utilisation of its cargo carrying units, by determining an optimum transportation sequence for routing of multiple vehicles within a fleet to visit tens, hundreds or thousands of locations, taking into account logical business rules for vehicles and stops such as order volume, loading capacity, time windows, service time, priority and the pre-allocation of particular stops to particular drivers. By defining various transportation events between stops enroute that take account of the various rules, and arranging the events in a sequence to define a route the optimum sequence for achieving a desired end result can be determined. The operation parameter defining the end result may be, for example, total operating cost, total driving time, total distance traveled (all of which will typically want to be minimised), probability of delivering goods on time, or a weighted sum of some or all of these. More complex sequences and event pools may take into account an optimum back-up fleet in case of unplanned vehicle maintenance or permanent vehicle replacement. Optimisation of this kind may determine how many vehicles should be included in the back-up fleet and where they should be located to minimise disruption to the fleet operation, for example.

j. "Knapsack problems". These are problems that can be considered in terms of filling a knapsack that can hold a total weight W or volume V with a combination of items from a list of n possible items each with weight $w_i$ or volume $v_i$ and value $(va)_i$ so that the value of the items packed into the knapsack is maximised. This problem has a constraint (that the total weight or volume of the items in the knapsack shall not exceed W and/or V), a linear or nonlinear objective function which sums the values of the items in the knapsack, and the added restriction that each item either be in the knapsack or not (a fractional amount of an item is not possible). Thus, each item can be represented by an event, and any combination of items/events can be arranged in any possible sequence representing the order in which the items in that combination are put into the knapsack. The end result of any sequence is the total value of the items; any combination that exceeds W and/or V is rejected, and the optimum sequence is identified by finding the non-rejected sequence that gives the maximum value. The surrogate modelling technique of the present invention allows the optimum sequence to be identified rapidly with no need to study all possible combinations of items. Knapsack problems are relevant to fleet management, for example, if the knapsack represents a cargo, passenger or warhead carrying unit and it is desired to load the unit to its limit for a particular parameter, represented by the value of the items.

k. Linking units. This is an extension of the knapsack problem. Transportation units such as rail wagons are linked together in a chain, and some parts of the chain may later need to be unlinked and removed (to deliver particular units to a customer, for example), and the rest of the chain then be reassembled, with perhaps new units added. Assembly, disassembly and reassembly of the units is time-consuming and hence costly, so it is desirable to optimise the ordering of the units within the chain to minimise these activities. The chain of units can be considered as a sequence of events, so that the optimum chain can be identified using the present invention.

In the case of a bomb plane releasing its payload it might have to do so in a specific order and constraints or variables might be time, fuel capacity, weather, time windows, etc.

l. Strategic wargaming. Running simulations at different strategic levels down to operational levels where outcomes of chains of events, for example, disabling bridges, to power plants, airports and other strategic units are run as scenarios where events are taking place or not. The modelling of discrete events is well-described mathematically. The method is suited for parallelised runs on a CPU cluster.

m. Use of a parallelised algorithm where each CPU searches all possible combinations around one variable in the case of setting up a Design of Experiments matrix and where the computer runs the surrogate model to cycle through all possible variable combinations for the desired result.

Embodiments of the invention will now be described in general terms applicable to any sequential combinatorial problem, such as those described above.

A specific example is then used to illustrate the use of the invention.

FIG. 1 shows a flow chart illustrating steps S1 to S9 of an embodiment of a method implementing the invention.

S1 Identify Combinatorial Sequential Process to be Optimised

The invention can be applied to any process that comprises a number of interchangeable events, the sequence of which requires optimising to attain the best end result. The process can be said to comprise n events (including the possibility of selecting those n from a larger pool, such as alternatives for some or all of the events), which can be combined in many or all possible sequences.

S2 Construct Master Model

In this example, a master model of the process is constructed, from which data to be used by the surrogate model can be obtained. An example of a suitable type of model is a finite element analysis model, but any suitably accurate model, generally a computerised model, can be used. The model will contain all parameters of relevance to the process, and will be configured to receive as an input any sequence of the events. The model then calculates a value of the final end result of the process that would be achieved for performing the events in the order of the input sequence. Also, it calculates the value of contributions to the end result of each of the events as it is performed; this contribution will typically depend on the position of the event within the sequence, and which, if any, events preceded it, (and possibly, followed it). The contributions are expressed in terms of the operation parameter of the process being modelled.

For example, if the operation parameter is a dimension of a component manufactured by the process, the contributions will therefore also be dimension values, for each event being the contribution to the total end dimension caused by that particular event.

If the operation parameter is the time taken to perform the process, the contributions will therefore also be time values, for each event being the length of time taken to perform that particular event.

Without the surrogate model, the optimisation process would require all possible sequences to be run through the master model, so that the sequence which gives the best end result can be identified. For a sufficiently detailed master model, this is prohibitively time-consuming for even a small number of events, since each sequence may take hours to run, and the total number of combinations will be large.

S3 Construct Surrogate Model

The surrogate model is a preferably a simplified approximation of the master model, in that it too takes the sequence of the events as an input, and calculates the end result of the process for performing the events in that sequence. However, the calculation involved is much simpler than the master model, so that all sequential combinations of interest can be calculated reasonably quickly (generally seconds or minutes instead of hours).

The surrogate model comprises a summing of the contribution of each event to the end result, to give an end result. The values of the contributions are determined using the master model, as discussed in the subsequent steps. The value of each contribution will generally depend on the position of the event in the sequence, and on any preceding events. The approximation to the master model arises in that, for each event in a given sequence, information may not be available for the contribution of the event at that particular position in that particular sequence. If not, the information is replaced by information relating to an arrangement as close as possible to the arrangement in question, according to an algorithm.

S4 Determine Design of Experiments (DoE)

To obtain the values of the contributions to be used in the surrogate model, it is necessary to run the master model one or more times. This gives information regarding values of the end results of the run sequences and of the contributions thereto of each event in the sequences. Since an aim of the invention is to reduce the number of computationally intensive runs of the master model, it is beneficial to choose a useful, information-rich selection of sequences to run through the master model to obtain a broad set of contributions for events in different arrangements. This plurality of sequences selected from the many possibilities will be referred to as the design of experiments (DoE). Thus, each sequence in the design of experiments is linked to information regarding values of the contributions to the end result for each event in each sequence, where, as discussed above, the contributions are in terms of the operation parameter.

As explained above, the surrogate model relies on an algorithm that, for each event in the sequence, determines which contribution from those available from the master model (the information linked to the design of experiments sequences) is to be used in the calculation of the end result. The algorithm follows a hierarchical or prioritised set of rules to determine which contribution of those available most closely matches the arrangement of the sequence being calculated. A close match will be one which corresponds to the present arrangement both in terms of the position of the event within the sequence and in terms of the preceding events. A weaker match will have a smaller number of the same preceding events, and/or will have the event at a different position in the sequence. Events matched in this way are termed "occurrences", where the goodness of the match is defined by the order and type of the occurrence; this is described in detail below with respect to the example embodiment. In determining the DoE, the user should decide which type of occurrence, or how good a match, is needed to give a sufficient level of accuracy to the optimised end result obtained from the surrogate model. For example, it may be decided that the match needs to be exact in terms of position of the event, and also to have the same preceding one event, or perhaps that the match of position is not important, but that the two events preceding the event in question must match. Once this has been determined, a calculation can be performed to find out how many and/or which sequences need to be run through the master model to provide enough combinations of events to match the desired level of occurrence detail. These sequences comprise the DoE.

Alternatively, it may be sufficient in some cases to merely run a random or pseudo-random selection of sequences through the master model. This collection of sequences can still be considered as the DoE, however, despite the lack of any particular design.

S5 Run DoE Sequences Through Master Model

Once the DoE has been established, each sequence in the DoE is run through the master model. The results of this are recorded, so that the contribution to the final result for each event in each DoE sequence is known. This provides the operation parameter information used in the calculations of the surrogate model.

S6 Construct Surrogate Model Priority List

The algorithm of the surrogate model follows the priority list for each event in a sequence run through the model. It takes the form of a hierarchy of matching to conditions between the event in question and the events included in the sequence of the DoE. The list begins with a requirement for a high degree of matching, and progresses through lower degrees of matching until no match is found. The algorithm therefore begins at the top of the list and searches the DoE for that high level of match with the event in question. If no match is found, it moves to the second condition on the list, and so on until a match is found or the end of the list is reached. When a condition has been selected by the algorithm in this way, the contribution previously calculated by the master model for the event in question in the DoE sequence in which the match is found is retrieved and included in the surrogate model summation used to determine the end result.

Therefore, it is necessary to establish a priority list appropriate for the process being optimised. The length of the list will impact on how long the surrogate model takes to calculate, since the execution time of the algorithm is proportional to the list length. However, a higher degree of matching at the top of the list will improve accuracy. It is not necessary to limit the highest degree of matching to that used when determining the DoE, since higher levels of match for some subsequences of events will be present in the DoE sequences, and using these where available will give a more accurate end result. Therefore, a useful priority list of general application that makes full use of any DoE is one which for any event, begins with searching for that event in the same position with all the same preceding events, whether the event is at the start or end of the sequence. When constructing the priority list, choices can be made as to whether matches in the position of the event within the sequence or in the preceding event or events are given higher priority. Examples of priority lists are given later.

S7 Run all Possible Sequences Through Surrogate Model

Once the surrogate model and its priority list have been constructed, and the information on the end result and contributions thereto have been calculated using the master model, the surrogate is used to run through all possible sequences. Each sequence is input to the surrogate model, which then, for each event in each sequence, implements the algorithm to establish the contribution to the end result for that event, and sums the contributions to find the end result for each sequence. Since the algorithm is a straightforward search and retrieve process, and the calculation for each sequence is a simple summation, the surrogate model can run each sequence very quickly, and in general it can be expected that only a few minutes will be needed for all the sequences to be examined.

In some cases, however, it may be possible to obtain a satisfactorily optimised sequence by running only some of the total number of possible sequences through the surrogate model. This is clearly faster than running all the sequences, so may be preferable in instances where time is very valuable; however, accuracy may be lost. A possible approach, particularly in cases where a desired optimum value of the end result of the process is known, is to run a subset of the sequences, and examine the various end results against the desired value. If no suitably close match is found, further sequences may be run, until a satisfactory end result is identified.

S8 Identify Optimum Sequence from Surrogate Model Results

After a result is obtained from the surrogate model for every sequence, the optimum sequence can be identified by comparing all the end results to find the one which is optimum having regard to the operation parameter defining the end result. Depending on the nature of the process, the optimum value of the operation parameter may be an end result with the smallest value, the largest value, or the value closest to a desired value. In some cases, the optimum value may conveniently be identified by comparison of the end results with some desired value of the operation parameter; in other cases the process will be such that the operation parameter should be minimised or maximised, such as performing a process as quickly as possible or obtaining the highest yield. The sequence giving the end result that corresponds to this optimum value is thus identified as the optimum sequence.

S9 Perform Process Using Optimum Sequence

The process can now be carried out using the sequence that has been identified as optimal, to achieve an optimum end result. However, if research into the process is ongoing, this step may perhaps not be undertaken, or may be delayed.

Figure 2:
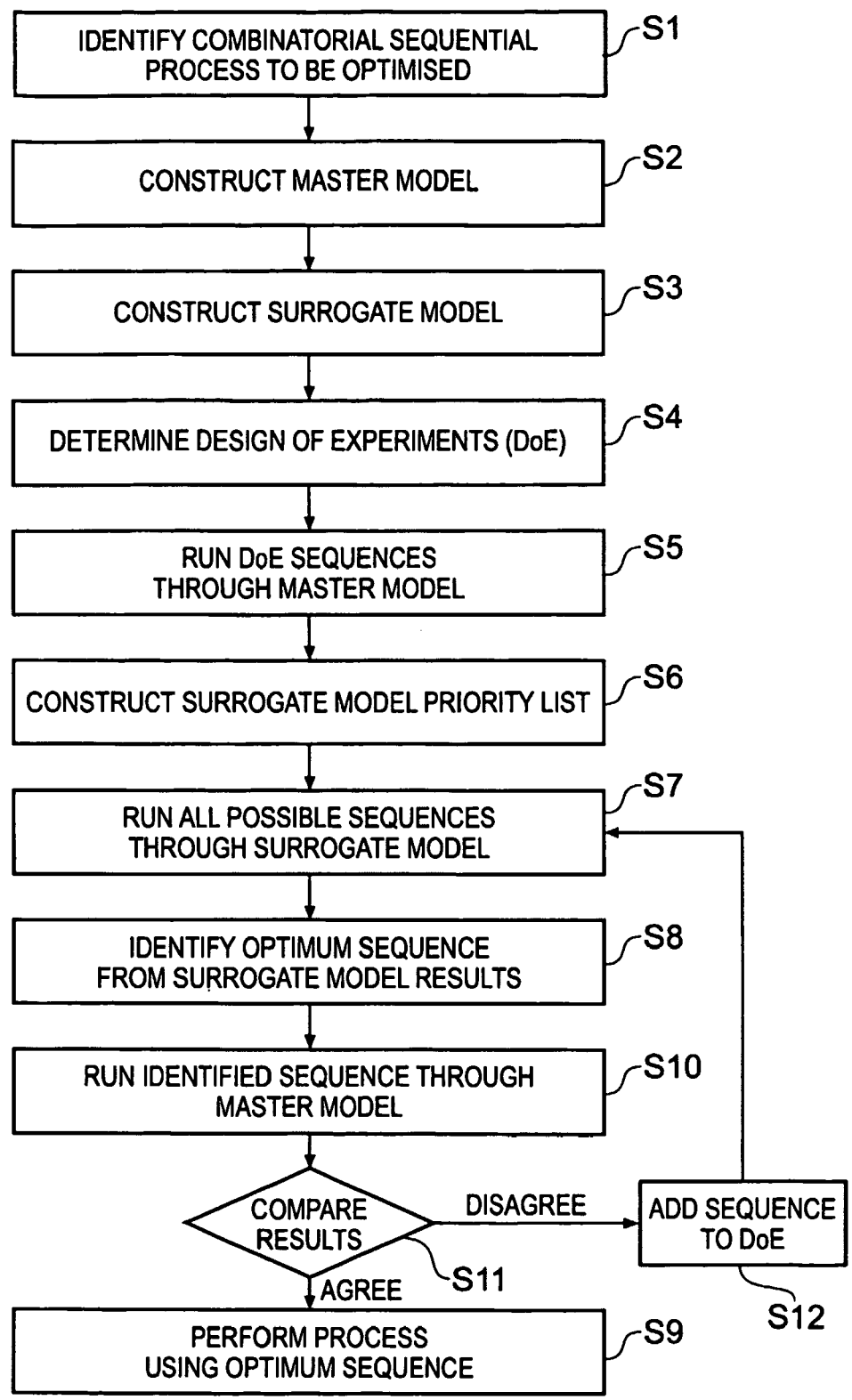
FIG. 2 shows a flow chart of steps in an alternative embodiment of a method according to the present invention.

FIG. 2 shows a flow chart of an alternative embodiment, comprising some additional steps that can be used to verify and if required improve the accuracy of the output of the surrogate model as regards identification of the optimum sequence. As in the FIG. 1 embodiment, the optimum sequence is identified from the surrogate model results in Step S8, whereupon the additional steps can be executed.

S10 Run Identified Sequence Through Master Model

The sequence identified as being optimum on the basis of the end results calculated by the surrogate model is run through the master model. This gives a value of the end result for that sequence which is known to be accurate to within the limits of the master model, which are higher than those of the surrogate model.

S11 Compare Results

The end result calculated by the master model for the identified optimum sequence is now compared to the end result for that sequence already calculated by the surrogate model. If the comparison is favourable, in that the two values of the end result agree to within an acceptable amount (which will depend on the nature of the process and the degree of accuracy required by the user), then the sequence is known to be optimal, and the method can proceed to Step S9 (perform process using optimum sequence) if desired. If the comparison is unfavourable, in that the two values do not agree to within the required limit, the identified sequence can be rejected as possibly not being optimal. In this case, the method proceeds instead to new Step S12.

S12 Add Sequence to DoE

The identified sequence has been run through the master model in Step S10, so that the contribution information used by the surrogate model to perform its calculations is now available for that sequence. Thus, the sequence can be added to the sequences in the DoE, just as if it had previously been run through the master model in Step S5. Then, the method returns to Step S7, and runs all possible sequences through the surrogate model again. This time, however, there is more information available to the surrogate model, since the DoE has been expanded. Hence, it is likely that the end results calculated by the surrogate model for each sequence are more accurate than previously, so that there is a better chance that the sequence identified in Step S8 really is optimal.

Again, this sequence can be put through the master model and the result compared with the result from the surrogate model to check accuracy. If the results do not agree, the sequence can be added to the DoE in Step S12, with the method returning again to Step S7. The loop of Steps S7, S8, S10, S11 and S12 can continue in this way until the desired level of agreement between the results of the surrogate model and master model is found, whereupon the method can proceed to Step S9. In this way, the accuracy of the optimisation is gradually improved. Also, this improvement is achieved in an efficient manner with regard to master model computation expense, since the additional sequences run through the master model in each Step S10 are likely to be close to optimal because they have been identified as such by the surrogate model. Thus the extra computation is concentrated in the area of interest, and accuracy is improved where it is most required.

It should be noted that to some extent the various steps described above can be performed in an order different from that depicted in FIGS. 1 and 2. In particular, Steps S2 to S6 can be performed in any order, as convenient to the user. Further, various of the steps can be reduced in scale, or left out altogether. For example, there may be no requirement to construct the master model, if a pre-existing model is available for use. This may be a model used previously in optimising the same process, a model used previously in optimising a similar process where the model is applicable to the present process, or a model supplied by or otherwise obtained from a separate source, whether or not this is done specifically for implementing the invention. This similarly applies to the surrogate model, so that the invention may or may not include constructing the surrogate model, and may be limited to using the surrogate model without constructing it. Also, the design of experiments may be determined for a specific optimisation process, or may be selected at random, or a previously defined design of experiments, preferably for the same or similar process, may be used, so that there is no need to define the DoE. Using pre-existing features in any of these ways will simplify and probably speed up the overall optimisation process.

It is expected that the master model, the surrogate model, the identification of the optimum sequence and the comparison between the results of the master model and the surrogate model will be implemented by computer software, for the sake of speed and convenience. For example, a computer program product may be provided that is capable of running the models, storing the design of experiments and the model results, and identifying the optimum sequence. A computer system may be provided that comprises memory for storing the design of experiments and the model results, and a processor for running the models, reading and writing data to and from the memory and identifying the optimum sequence. However, a computer implementation is optional, and in some cases it may be preferred to implement some or all of these features in other ways, such as by electronic hardware, or perhaps by hand.

Further with regard to computer implementations of the invention, further increases in speed can be obtained by adopting a parallel approach. The DoE can usefully be determined using a computer to run a selection of sequences through the master model (as discussed in more detail below with respect to a more detailed example) until a desired range of events has been covered and the respective contributions calculated. In a case where an event incorporates more than one variable, for example where a particular step in a process can be performed at more than one temperature and in more than one direction, a separate computer processor can be dedicated to each variable. To determine the DoE, each processor runs sequences around one of the variables while the other variables are kept constant. This provides a more rapid way of determining the DoE while still allowing all variables to be considered, and can also allow simpler master models to be used, since each will only have to take account of one variable.

Similarly, parallel processors can be used for running the plurality of sequences through the surrogate model, where each processor is dedicated to sequences involving different values of a single parameter. Again, this can allow simpler versions of the surrogate model to be used, and allows the optimum sequence to be identified more quickly than if a single processor runs all sequences through the surrogate model.

Detailed Example I

The invention will now be further described with reference to a more detailed example.

Consider a process comprising six steps. The six steps can be performed in any order, and each step can be performed in one of two ways (such as forwards or backwards, or at a first or second temperature). The ordering and the choice of which way to perform each step modify the end result of the process. Let this end result be defined by an operation parameter X, and the desired nature of the end result be such that the operation parameter has an optimal value X=0. In other words, the operation parameter is to be minimised.

Each step or event is given a label, let this be the numbers 1-6. Positive and negative values of these numbers will be used to denote the two ways of performing each event. A sequence of the steps can thus be represented by, for example [−6, 5, 3, 1, −4, 2], in which the individual numbers are the labels designating the particular events, and the position of each number in the sequence represents the position that that event is performed in within the sequence.

A master model in the form of a finite element (FE) model is created that to describes the sequential process, and which can consider each event in any position in the sequence, and in either way of performing the events. The model takes as input the sequence and produces a diagram representing the evolution of the operation parameter X during the process. It can calculate the final value of X for any event combination, as well as the contribution to X caused by each individual event.

The goal of the optimisation process is to minimise the value of X by changing the sequence of events. There are six variables (one for each position in the sequence), each of which can take 12 non-numerical values (6 for the first way of performing each event and 6 for the second way). This gives a total of $2^6 \times 6! = 46080$ combinations. According to some conventional optimisation techniques for sequential combinatorial problems it is necessary to run all these combinations through the FE model, and select the sequence with the least value of X. However, this is impractical since one combination takes 32 hours to compute. Other available combinatorial optimisation methods described in the literature, such as integer programming, graphs, branch and bound, and binary trees [2] are unable to reduce the number of combinations that must be calculated to any great extent. The present invention significantly reduces the time required to achieve the result by using a surrogate model that computes much more rapidly than the FE model, and is used to reduce the number of FE runs required. The surrogate model uses data obtained from FE runs, so that some FE runs are necessary, but the surrogate model can approximate the FE model using data from a much smaller number of runs than the total number of possible combinations.

To develop the surrogate model, the total value of X can be described simply as the sum of the contributions to X caused by the six individual events:

$$X = \sum_{i=1}^{6} (x_i) \qquad (1)$$

where $x_i$ is the contribution caused by event i in the sequence. The FE model can calculate the contribution of each event, so can provide the information needed by the surrogate.

The contribution caused by any individual event will depend on the position of the event in the sequence, in which of the two possible ways the event is performed, and any previous events. If the event occurs first in the sequence the contribution caused is independent of subsequent event. This will be termed here as a main effect. The main effect for an event e will be denoted as $M_e$. For instance, the example sequence given above gives information about $M_{-6}$, since −6 is the first event in this sequence. Overall, there are six possible first event each with two possible ways of being performed, which gives a total of twelve possible values of the main effect. These can be determined by twelve runs of the FE model. There is no need to run the whole sequence; the first event from twelve runs that each contain a different event and performance combination as the first event in the sequence will provide complete information about all possible main effects.

A particularly simple model as a candidate for the surrogate is one in which the final value of X is assumed to be the sum of the main effects:

$$X = \sum_{i=1}^{6} M_{e_i} \qquad (2)$$

where $e_i$ is event e at the ith place in the sequence. As an example, the model gives the value of X for the sequence [−6, 5, 3, 1, −4, 2] as $X = M_{-6} + M_5 + M_3 + M_1 + M_{-4} + M_2$. This model is based on a system without memory, in which no account is taken of the effect on the present event of any previous events. It assumes the same behaviour for all places in the sequence as for the initial event, by substituting all $x_i$ for i=2, 3, 4, 5, 6 with the corresponding main effects. This means that these coefficients depend only on the event, and not on the place they have in the sequence. No consideration is given to the effect of what may have happened internally in the process due to previous events. This model meets the desired aim of a low number of FE runs to provide all the information needed to run every possible sequence through the surrogate model, because it requires only twelve runs. However, typically a system does not behave as a non-memory system; the contributions to the end results caused by a given event varies with its place in the sequence. Therefore, a more accurate model is:

$$X = \sum_{i=1}^{6} (M_{e_i} + \Delta(e, i)) \qquad (3)$$

where $\Delta(e,i)$ is the improvement to the accuracy caused by including the effect of the position of the event in the sequence. In this case, the contributions $x_i = f(e,i)$ are functions of the event and position.

To enable the system memory to be included in the optimisation, definitions of the order and the type of contribution to the overall end result of any individual event, referred to as occurrences, are introduced. To describe the contribution at position i, the occurrences are defined as follows:
  (i) First order terms of type 1, which ignore any contribution of previous events, i.e. they represent a system with no memory. However, they do take into account the effect of the position within the sequence. The main effects defined earlier are first order terms of type 1, but only when they are used to describe the displacement at position 1.
  (ii) First order terms of type 2 also ignore previous events, and also they ignore the effect of the position. For example, the model based on equation (2) incorporates only these terms. In $X = M_2 + M_{-5} + M_6 + M_{-1} + M_3 + M_{-4}$, $M_2$ is a first order term of type 1, while the remainder are due to type 2 occurrences, since the contributions $M_{-5}$, $M_6$, $M_{-1}$, $M_3$ and $M_{-4}$ come from simulations where the events −5, 6, −1, 3 and −4 occurred in position 1 of the sequences run through the FE model, but elsewhere in this run.
  (iii) Second order terms of type 1 allow for the position of an event in a sequence and the immediate history of the sequence (i.e., the event immediately preceding the event i under consideration). Occurrences of second order exist only if $i \geq 2$.
  (iv) Second order terms of type 2 take account of the previous event, but ignore the importance of the position of the pair of events in the sequence.
  (v) Third order terms, which exist only for $i \geq 3$, incorporate the two events that are immediately before the one under consideration.
  (vi) And so on for higher orders.

In the following, the order of an occurrence is designated by an appropriate numerical subscript and the type is designated by primes. Therefore, occurrences of kth order and type one are denoted as $R_k'(v,i)$, where v is a vector consisting of the events at positions $[e_{i-k+1}, \ldots, e_{i-1}, e_i]$, that hence include the k−1 events preceding the present event. Those of type two will have a double prime.

Consider k=1 and type one: sequence 20 gives information about the following occurrences of first order (where the first number of each pair represents the event, and the second number is its position in the sequence): $R_1'(2, 1) = M_2$; $R_1'(-5, 2)$; $R_1'(6, 3)$ $R_1'(-1, 4)$, $R_1'(3, 5)$ $R_1'(-4, 6)$. It contains information about the change to X caused by the occurrence of event e at position i in the sequence. It is straightforward to create a design of experiments (DoE) that runs the FE model enough times to fill a matrix comprising all the first order type one occurrences $R_1'$ for e=−6, . . . , −1, 1 . . . 6; i=1, . . . , 6. Such a design requires 18 runs.

To describe a system with memory, it is necessary to account for the effect of present and past occurrences, rather than only present occurrences such as $R_1'$. Such occurrences are of second and higher order. To simplify the model, it is reasonable to assume that when considering the last event in the sequence the effect on its displacement caused by, say, the penultimate event will be more important then the first (so that very high order occurrences can be neglected). Furthermore, it may be postulated that sub-sequences of several events will have broadly similar effects wherever they occur in the sequence (so that type two occurrences are sufficient for high order occurrences). Using these ideas it is possible to build approximations to the effect of any event, using information from runs that have been previously carried out. This information comprises the DoE. The process is as follows:
  1. Overall, aim to predict the contribution to X after each event, and finally sum them up to obtain a total value of X. Initially X=0.
  2. Let zp be the sequence of interest. For example, zp=[6, 3, −5, 4, −2, 1].
  3. Start with i=1 (first event in sequence) and then increment it in due course.
  4. The highest possible order of occurrence is i.
  5. Create vector zp1=[1: i] that contains the first i elements of zp. For instance for i=3; zp1=[6, 3, −5].
  6. Let k=1.
  7. Create vector zp2=zp1[i−k+1: i] that takes the last i−k+1 elements of zp1.
  8. Search DoE for zp2 so that the last element of zp2 appears at ith position of a sequence in the DoE. If found, take the value of the corresponding contribution $x_i$ and go to 10, otherwise continue. The contribution found is an occurrence of order i and type 1.
  9. Search DoE for zp2 anywhere in the DoE regardless of position in the sequences. If found, take the value of the corresponding contribution $x_i$ and go to 10. The contribution found is an occurrence of order i and type 2.
  10. $X = X + x_i$.
  11. if i=ep then STOP. The end of the sequence has been reached. In the example presented here, ep=6 which corresponds to 6 events per sequence.
  12. i=i+1.
  13. go to step 4.

This process is very much faster to compute than a run of the FE model. Thus, using the results of a relatively small number of FE runs to populate the DoE, the surrogate model can rapidly run through all the possible sequences and identify the sequence that gives the most desirable value of X.

To illustrate the idea of using these occurrences, consider a model based on terms up to $R_2'$:

$$X = M_{e_i} + \sum_{i=2}^{6}(M_{e_i} + \Delta R_1'(v, i) + \Delta R_2'(v, i)), \quad (4)$$

where $\Delta R_1'(v,i)=R_1'(v,i)-M_{e_i}$; $\Delta R_2'(v,i)=R_2'(v,i)-M_{w_i}$; i is the position in the sequence; and $v=[e_{i-k+1}, \ldots, e_{i+1}, e_i]$, where k=1 and 2, respectively.

As an example, the sequence [2, −5, 6, −1, 3, −4] provides information about the following occurrences of second order: $R_2'(2, -5, 2)$; $R_2'(-5, 6, 3)$; $R_2'(6, -1, 4)$; $R_2'(-1, 3, 5)$; $R_2'(3, -4, 6)$, where the last number in each group is the position in the sequence of the two events represented by the first two numbers. 180 runs of the FE model are needed to fill the whole $R_2'$ DoE matrix, and this makes its use unattractive. Instead, it is possible to compromise by using a DoE that fills the whole $R_2''$ matrix instead. To ensure that all occurrences of second order and type two exist, 27 FE runs are required. It can be shown for many processes that this approximation, which ignores where the sub-sequence pairs have occurred, does not cause a great loss of accuracy. Moreover, some $R_2'$ pairs will be available from the matrix, and can be used if available. Therefore, the terms $R_2'$ in (4) can be replaced by $$\overline{R}_2(v, i) = \begin{cases} R_2'(v, i) \text{ if it exists in the } DoE \\ R_2''(v) \text{ if the above does not exist in the } DoE \\ 0 \text{ if neither of the above exists in the } DoE \end{cases} \quad (5)$$

Thus, the second order terms are used wherever possible, and only replaced by lower order terms if unavailable. This small loss in accuracy is balanced by the reduction in the number of FE runs needed for the DoE.

Although the DoE is designed to include all possible occurrences of $R_2''(v)$, for some events and positions it will contain occurrences of third order and higher, which may be used to improve the accuracy further. Thus, equation 5 can be generalised to:

$$H(i) = \begin{cases} \overline{R}_i \text{ if } \overline{R}_i \in DoE, & \text{else} \\ \overline{R}_{i-1} \text{ if } \overline{R}_{i-1} \in DoE, & \text{else} \\ \vdots \\ M_{e_i} \text{ if } M_{e_i} \in DoE, & \text{else} \\ M_e \text{ if } M_e \in DoE, & \text{else} \\ 0 \end{cases} \quad (6)$$

and the total value of X is defined as $$X = \sum_{i=1}^{n} H(i) \quad (7)$$

where n is the total number of events in the sequence; n=6 in the present example. Equation 7 is a more general form of equation 4 that finds the sum of the combination of the highest occurrences of lowest type to calculate the predicted value for X for a given event and sequence position.

This model can be applied to any number of variables or events n, bearing in mind that the highest order of occurrence is equal to the number of variables. The model exhibits some learning properties, in the sense that it will always produce a prediction if there is at least one point in the DoE. If more FE runs are performed, the DoE grows in size, and the predictions will become more accurate. In the limit when all possible combinations have been tested by the FE model it reproduces trial data from the process exactly. This feature allows the surrogate model to be used with any number of points in the DoE, giving the freedom for the latter to grow or stop growing, according to the desired accuracy of the model. For examples studied such as the one here with six events, experience suggests that the existence of the complete $R_2''$ set is enough to ensure a good fit to the existing data.

It is clear that once contribution data has been calculated from sufficient FE runs as defined by the DoE, such a model requires very little computation, and this enables all possible combinations to be examined by the surrogate model and the best one selected. To test the accuracy, this best prediction can then be checked by running its sequence through the FE model. This FE run can then be added to the DoE, making to further predictions of the surrogate model more accurate. Another full search of the combination can then be performed by the surrogate model, using all the DoE information, including that from the latest FE run and so on, until successive models produce the same or sufficiently similar results.

Continuing with the present example of a six event process, and following the conclusions reached above, it is possible to construct a table of a DoE corresponding to 27 runs of the FE model, that ensures that all $R_2''$ occurrences are included. The DoE may, for example, be constructed by considering all possible 46080 combinations and selecting the first set that provides at least one example of all $R_2''$ occurrences. One way to achieve this is to run six nested loops, each one running through the values −6, −5, −4, −3, −2, −1, 1, 2, 3, 4, 5, 6 and selecting the sequences that obey the following rule $|A|\neq|B|\neq|C|\neq|D|\neq|E|\neq|F|$ where A, B, C, D, E and F are the six nested loops variables. Each sequence is recorded, and when at least one example of each $R_2''$ occurrence has been found, the DoE generation stops. This produces a DoE that contains the first set of sequences that guarantees that all $R_2''$ occurrences are tested. This is a particularly simple way of generating the DoE, but it should be noted that the result is not necessarily the optimal DoE, nor the smallest possible DoE, although the smallest possible DoE is not expected to be much smaller.

Each sequence in the DoE is run through the FE model. For each event in each sequence of the DoE, the contribution to X is calculated from the difference of the accumulated value of X at the end and beginning of a sequence as calculated by the FE model.

For illustration purposes, consider the sequence [6, 3, −5, 4, −2, 1], and apply the model to it:

1. X=0.
2. i=1: For position number 1, the highest order of occurrence is 1 so check if there is a main effect for 6 in the DoE points. Assume that one is found. The to contribution for a main effect of 6 is extracted from the calculated data, and the value is added to X, and now $X=M_6$.
3. i=2: The highest order of occurrence is 2, so look for the pair (6, 3) within the DoE at position 2 (an occurrence of type 1 is sought first). If there is no match, so next look for occurrences of type 2, regardless of position. Assume a match is found, so that the corresponding contribution is added to X, so that $X=M_6+R_2''(6, 3)$.
4. i=3: The highest order of occurrence is 3, so look for the sub-sequence (6, 3, −5) within the DoE at position 3 (again, an occurrence of type 1 is sought first). If the subset cannot be found in the DoE, check for this triple anywhere in the DoE. Assume this fails, indicating that there is no such third order occurrence of either type 1 or type 2. Next, reduce the subset by truncating the farthest event, which presumably has least effect on the deflection generated at position 3. The subset becomes (3, −5). Again, check first for its occurrence of type 1, i.e., such that event −5 stands at position 3 and event 3 stands at position 2. Say that a match is found, and the corresponding contribution is added to the value of X, so that $X=M_6+R_2'(6, 3)+R_2'(3, −5, 3)$.

5. i=4: The highest order of occurrence is 4, so look for the sub-sequence (6, 3, −5, 4) within the DoE at position 4, for an occurrence of type 1. There is no match, so look for occurrences of type 2, which cannot be found either. Next, truncate the subset to (3, −5, 4) and look first for occurrences of type 1. There is a match in run 18, so add the appropriate contribution on the $R_3'$ term to the value of X, so that $X=M_6+R_2''(6, 3)+R_2'(3, −5, 3)+R_3'(3, −5, 4, 4)$.

6. i=5: The highest order of occurrence is 5, so look for the sub-sequence (6, 3, −5, 4, −2) within the DoE at position 5, for an occurrence of type 1. Assume none is found, and neither is a type 2 occurrence, so truncate and look for (3, −5, 4, −2). Assume further that the search again fails for both type 1 and type 2. Truncate further to (−5, 4, −2). Again no match is found for either type. Truncate to (4, −2). There is no type 1 occurrence, but say a type 2 occurrence appears in the DoE. Add the contribution to X, so that $X=M_6+R_2''(6, 3)+R_2'(3, −5, 3)+R_3'(3, −5, 4, 4)+R_2''(4, −2)$.

7. i=6: The highest order of occurrence is 6, so look for the sub-sequence (6, 3, −5, 4, −2, 1) within the DoE at position 6. Assume, unsurprisingly that it is not found. Go through the same procedure as in the previous stage, checking for occurrences of type 1 and 2, of the following subsets (3, −5, 4, −2, 1); (−5, 4, −2, 1); (4, −2, 1). Assume none is found. Finally, assume that a search for (−2, 1) anywhere in the DoE, regardless of position, finds a match in run 14. Add the displacement to X, so that $X=M_6+R_2''(6, 3)+R_2'(3, −5, 3)+R_3'(3, −5, 4, 4)+R_2''(4, −2)+R_2''(−2, 1)$.

Using the above algorithm, all 46080 possible combinations may be calculated in less than 5 minutes on 800 MHz Pentium III machine, using a MATLAB code. A code written in C or FORTRAN would produce results much faster.

The present invention has been advantageously applied to the optimisation of a real process comprising a sequence of six events. An optimised value of X, and the corresponding sequence have been determined with only 28 runs of an FE model, out of a possible 46080 sequence combinations. Tests of the identified sequence in the FE model have confirmed that the identified value is accurate. Thus, the computational expense needed in planning processes of this type is greatly reduced, without significant loss of accuracy.

Detailed Example II

The invention will now be further described with reference to a specific example, that of the welding of a vane in the inner ring of a gas turbine tail bearing housing (TBH).

Figure 3:
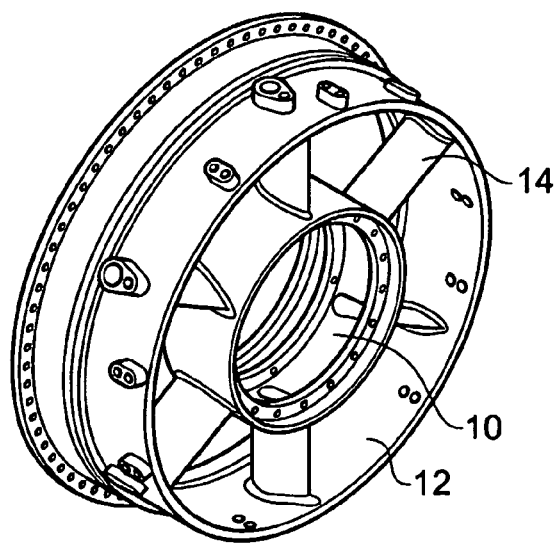
FIG. 3 shows a perspective view of a gas turbine tail bearing housing, to the manufacture of which an embodiment of the present invention can be applied.

FIG. 3 shows a perspective view of a typical TBH. It is a crucial component for the mounting of a jet engine to the body of an aircraft. Its major structural details are shown in FIG. 3, and comprise an inner ring 10, an outer ring 12 encompassing the inner ring 10, and a plurality of vanes 14 extending radially between the inner ring 10 and the outer ring 12. The vanes 14 are usually welded to the rings 10, 12 using gas tungsten arc welding, frequently known as TIG welding.

Figure 4:
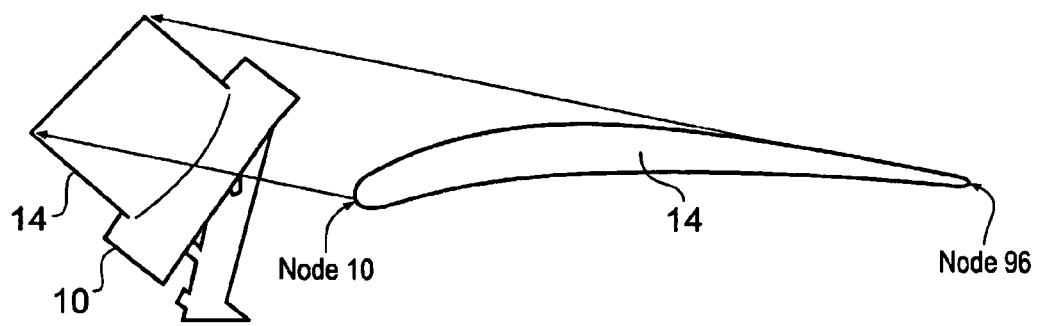
FIG. 4 shows perspective and cross-sectional views of parts of the housing of FIG. 3.

The inner ring 10 and the vanes 14 are both clamped in a desired position during the welding of these components. However, due to internal stresses generated by heating, the vane deforms. The welding causes a contraction which occurs when the melted material in the weld pool is cooled. This causes stresses of large magnitude to be distributed throughout the component and also imparts deformations to the workpiece. This can be measured by the displacement of the two nodes or tips of the vane at the end of the vane opposite to the welding event. FIG. 4 shows these nodes (Node 10 and Node 96) indicated on a perspective view of a vane 14 and associated portion of the inner ring 10, and on a cross-sectional view of the vane 14. Node 10 is the front tip at the leading edge of the vane 14 and Node 96 is the back tip at the trailing edge of the vane 14. The deformation is undesirable.

The welding parameters such as weld speed and power are defined by the welding process itself and can only be altered to a small extent to reduce the deformation. The alternative approach of the present invention is to consider the welding process as a sequential combinatorial process, by dividing the path of the welding around the join between the vane and inner ring into smaller intervals. Then, the sequence in which these individual welds should be performed to cause minimal or no deformation can be determined.

Figure 5:
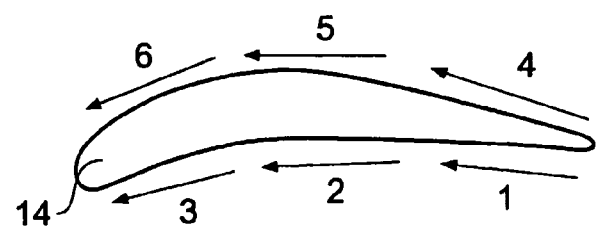
FIG. 5 shows a cross-sectional view of a vane forming part of the bearing of FIG. 3, with arrows indicating paths along which the vane is welded to an inner ring of the bearing.

FIG. 5 shows a cross-section of the base of the vane 14 that has to be welded to the inner ring 10. The welding takes place around the contour of this representation, i.e. around the edge of the vane. The contour has been divided into six welding paths or events, as shown by the arrows in the Figure. The welding is performed on one path at a time, and preferably there is five second gap between the end of one weld and the beginning of the next, to allow for repositioning of the welding tool. The numbers 1-6 labelling the arrows in FIG. 5 are used to denote the welding event represented by the adjacent arrow, and not the order in which the paths are welded. The welding can be performed in any order. In the following description, a particular notation is adopted to describe the welding order. The numbers 1 to 6, representing the paths of FIG. 5, are listed in the order in which the corresponding paths are welded. Each path can be welded in either direction; a positive value in the notation indicates welding in the direction of the arrow of FIG. 5, and a negative value indicates welding in the opposite direction.

Figures 6, 7:
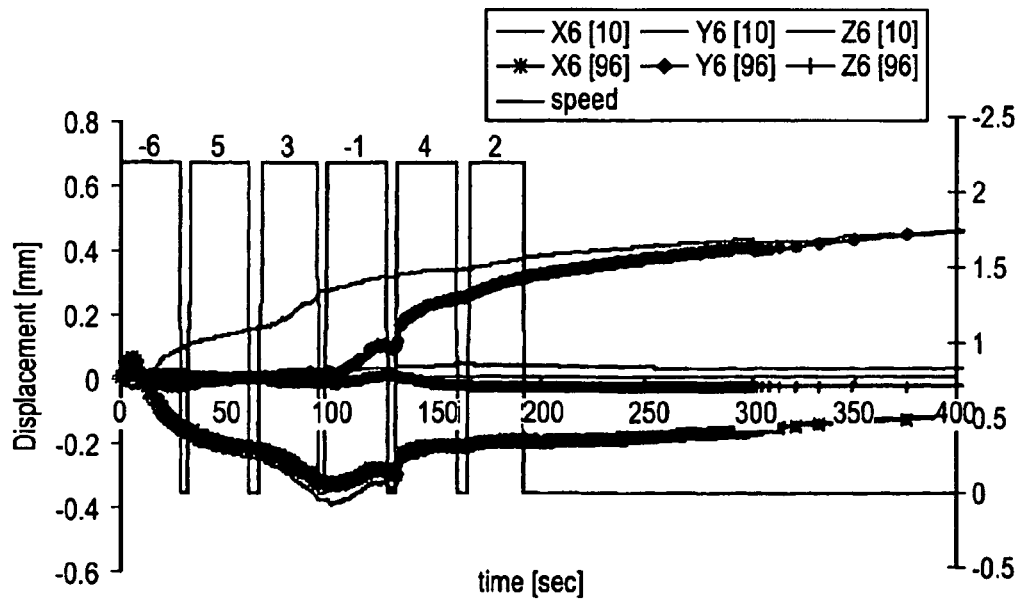
FIG. 6 shows a table of various example sequences in which the paths of FIG. 5 can be welded.
FIG. 7 shows graphs of the variation in displacement of parts of the vane during the welding process.

FIG. 6 presents a table showing this notation used to describe some possible welding sequences. Four sequences (labelled 1, 2, 6 and 20 in the left-hand column) are shown for illustration. The central column shows the welding sequences. In the header row of this column, labels 1 to 6 designate the six places or positions in a welding sequence. Each welding sequence is listed in this column, and contains the names 1-6 of the welding events as given in FIG. 5, with a minus sign corresponding to the opposite weld direction as explained. The dashed lines running vertically down the central column represent the five second gaps, used to change and reposition the welding tool. Thus, the numbers in the heading columns correspond to the order in the sequence in which the welds have been carried out, and the numbers in the rows below represent the individual welding events. The left-hand column shows pictorial representations of the direction and sequential position of the welding events in each sequence, where the numerical labels refer to the sequential position of each weld (in contrast to the labels in FIG. 5, which refer to the welding event of the adjacent arrow).

A master model in the form of a finite element (FE) model is created that describes the sequential welding process, and which can consider each welding event in any position in the sequence, and in either direction. The model takes as input the welding sequence and produces a displacement diagram over the welding process. It can calculate the total displacement at Node 10 and Node 96 for any event combination, as well as the contributory displacement caused by each individual welding event. As an example, these displacements have been calculated for welding sequence 6 of FIG. 6. The analysis shows that the X component of the displacement is of most interest for optimisation, as it is the most significant and changes in both directions (plus and minus). Component Z is an order of magnitude lower than X and therefore does not have significant influence on the resultant displacement. Component Y only changes in the positive direction, and cannot be compensated for is by changing the welding sequence.

FIG. 7 shows a graph of the results of the model, including the three components of the displacement at node 10 for welding sequence number 6. Also shown is a curve labelled 'speed' that shows the speed of the welding tool, and may be used to visualise and distinguish between the six welding processes and the five second cooling gaps. The welding completes after 193 seconds and then the weld is cooled with clamps on until 300 seconds, when the clamps are released and the cooling continues to room temperature.

Figure 8:
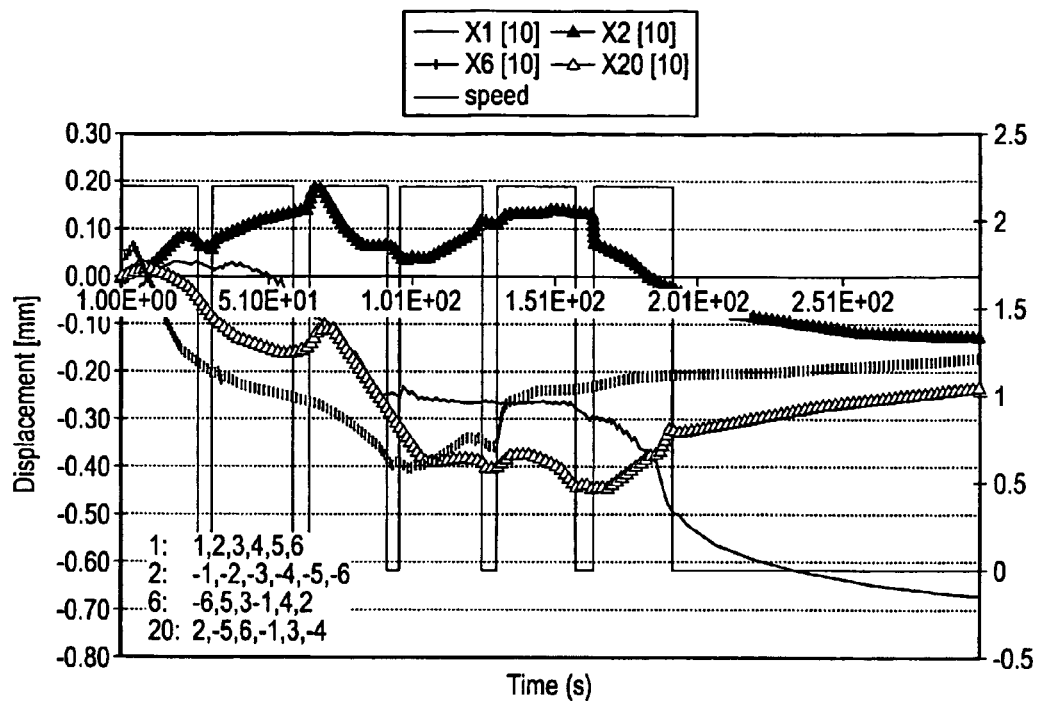
FIG. 8 shows graphs of the variation in displacement of a part of the vane during the welding processes for the sequences of FIG. 6.

FIG. 8 shows graphs of the displacement component X for sequences 1, 2, 6 and 20 from FIG. 6 calculated using the FE model. From this it is clear that variation of the welding sequence can significantly change the displacement, and therefore can be used for optimisation purposes. Therefore, the aim of the present example is to optimise the welding sequence so as to minimise the displacements while the components are clamped. The goal is to reduce the final displacement by changing the welding sequence. There are six variables (one for each welding position), each of which can take 12 non-numerical values (6 for one direction and 6 for the opposite). This gives a total of $2^6 \times 6! = 46080$ combinations. According to some conventional optimisation techniques for sequential combinatorial problems it is necessary to run all these combinations through the FE model, and select the welding sequence with the least displacement. However, this is impractical since one combination takes 32 hours to compute. Other available combinatorial optimisation methods described in the literature, such as integer programming, graphs, branch and bound, and binary trees [2] are unable to reduce the number of combinations that must be calculated to any great extent. The present invention significantly reduces the time required to achieve the result by using a surrogate model that computes much more rapidly than the FE model, and is used to reduce the number of FE runs required. The surrogate model uses data obtained from FE runs, so that some FE runs are necessary, but the surrogate model can approximate the FE model using data from a much smaller number of runs than the total number of possible combinations.

To develop the surrogate model, the total displacement D can be described simply as the sum of the displacement caused by the six individual welds and the cooling involved:

$$D = \sum_{i=1}^{6} (d_i + d_i^c) + d^c, \tag{1}$$

This is a superposition of $d_i$, the displacement caused by weld i in the welding sequence; $d_c$, the displacement caused by the cooling stage after each weld; and $d^c$, the displacement caused by the final cooling stage. To simplify matters, the cooling displacement will be ignored to begin with, so that equation (1) becomes:

$$D = \sum_{i=1}^{6} d_i \tag{2}$$

Test runs of the FE model with and without the cooling have shown that this assumption does not bring a great loss of accuracy, because the contributions to the overall displacement from the welding process overwhelmingly exceed those from the cooling processes. The FE model can calculate the displacement caused by each weld, so can provide the information needed by the surrogate.

The displacement caused by any individual weld will depend on the position of the weld in the sequence, the weld direction, and any previous welds. If the weld occurs first in the sequence the displacement caused is independent of subsequent welds. This will be termed here as a main effect. The main effect for a welding event w will be denoted as $M_w$. For instance, runs 1, 2, 6 and 20 discussed above give information about $M_1$, $M_{-1}$, $M_{-6}$ and $M_2$ respectively, since 1, −1, −6 and 2 are the first weld events in these sequences. Overall, there are six possible first welds each with two possible directions, which gives a total of twelve possible values of the main effect. These can be determined by twelve runs of the FE model. There is no need to run the whole welding sequence; the first weld from twelve runs that each contain a different welding position and direction combination as the first event in the sequence will provide complete information about all possible main effects.

A particularly simple model as a candidate for the surrogate is one in which the final displacement is assumed to be the sum of the main effects:

$$D = \sum_{i=1}^{6} M_{w_i} \tag{3}$$

where $w_i$ is welding event w welded at ith place in the welding sequence. As an example, the model gives the displacement for sequence 20 in FIG. 6 as $D = M_2 + M_{-5} + M_6 + M_{-1} + M_3 + M_{-4}$. This model is based on a system without memory, in which no account is taken of the effect on the present weld of any previous welds. It assumes the same behaviour for all places in the sequence as for the initial weld, by substituting all $d_i$ for i=2, 3, 4, 5, 6 with the corresponding main effects. This means that these coefficients depend only on the welding event, and not on the place they have in the welding sequence. No consideration is given to the effect of what may have happened internally in the system due to previous welds, such as displacement due to internal stresses and thermal deformations. This model meets the desired aim of a low number of FE runs to provide all the information needed to run every possible weld sequence through the surrogate model, because it requires only twelve runs. However, the welding process does not behave as a non-memory system; the displacements caused by a given welding event varies with its place in the welding sequence. Therefore, a more accurate model is:

$$D = \sum_{i=1}^{6} (M_{w_i} + \Delta(w, i)) \qquad (4)$$

where $\Delta(w,i)$ is the improvement to the accuracy caused by including the effect of the position of the weld event in the sequence. In this case, the displacements $d_i=f(w,i)$ are functions of the welding event and position.

To enable the system memory to be included in the optimisation, definitions of the order and the type of contribution to the overall displacement of any individual event, referred to as occurrences, are introduced. To describe the displacement at position i, the occurrences are defined as follows:

(vii) First order terms of type 1, which ignore any contribution of previous weld events, i.e. they represent a system with no memory. However, they do take into account the effect of the position within the sequence. The main effects defined earlier are first order terms of type 1, but only when they are used to describe the displacement at position 1.

(viii) First order terms of type 2 also ignore previous weld events, and also they ignore the effect of the position. For example, the model based on equation (3) incorporates only these terms. In $D=M_2+M_{-5}+M_6+M_{-1}M_3+M_{-4}$, $M_2$ is a first order term of type 1, while the remainder are due to type 2 occurrences, since the contributions $M_{-5}$, $M_6$, $M_{-1}$, $M_3$ and $M_{-4}$ come from simulations where the welding events $-5$, $6$, $-1$, $3$ and $-4$ occurred in position 1 of the welding sequences run through the FE model, but elsewhere in this run.

(ix) Second order terms of type 1 allow for the position of a welding event in a sequence and the immediate history of the sequence (i.e., the welding event immediately preceding the weld i under consideration). Occurrences of second order exist only if $i \geq 2$.

(x) Second order terms of type 2 take account of the previous welding event, but ignore the importance of the position of the pair of events in the sequence.

(xi) Third order terms, which exist only for $i \geq 3$, incorporate the two welding events that are immediately before the one under consideration.

(xii) And so on for higher orders.

In the following, the order of an occurrence is designated by an appropriate numerical subscript and the type is designated by primes. Therefore, occurrences of kth order and type one are denoted as $R_k'(v,i)$, where v is a vector consisting of the welding events at positions $[w_{i-k+1}, w_{i-1}, w_i]$, that hence include the k−1 events preceding the present event. Those of type two will have a double prime.

Consider k=1 and type one: sequence 20 gives information about the following occurrences of first order (where the first number of each pair represents the weld event, and the second number is its position in the sequence): $R_1'(2, 1)=M_2'$; $R_1'(-5, 2)$, $R_1'(6, 3)$; $R_1'(-1, 4)$; $R_1'(3, 5)$; $R_1'(-4, 6)$. It contains information about the change to the displacement caused by the occurrence of welding event w at position i in the welding sequence. It is straightforward to create a design of experiments (DoE) that runs the FE model enough times to fill a matrix comprising all the first order type one occurrences $R_1'$ for w=−6, . . . , −1, 1 . . . 6; i=1, . . . , 6. Such a design requires 18 runs.

To describe a system with memory, it is necessary to account for the effect of present and past occurrences, rather than only present occurrences such as $R_1'$. Such occurrences are of second and higher order. To simplify the model, it is reasonable to assume that when considering the last weld in the sequence the effect on its displacement caused by, say, the penultimate weld will be more important then the first (so that very high order occurrences can be neglected). Furthermore, it may be postulated that sub-sequences of several welds will have broadly similar effects wherever they occur in the sequence (so that type two occurrences are sufficient for high order occurrences). Using these ideas it is possible to build approximations to the effect of any weld, using information from runs that have been previously carried out. This information comprises the DoE. The process is as follows:

14. Overall, aim to predict the deflection after each event, and finally sum them up to obtain a total deflection. Initially D=0.
15. Let xp be the sequence of interest. For example, xp=[6, 3, −5, 4, 2, 1].
16. Start with i=1 (first event in sequence) and then increment it in due course.
17. The highest possible order of occurrence is 1.
18. Create vector xp1=[1: i] that contains the first i elements of xp. For instance for i=3; xp1=[6, 3, −5].
19. Let k=1.
20. Create vector xp2=xp1[i−k+1:1] that takes the last i−k+1 elements of xp1.
21. Search DoE for xp2 so that the last element of xp2 appears at ith position of a sequence in the DoE. If found, take the value of the corresponding displacement $d_i$ and go to 10, otherwise continue. The displacement found is an occurrence of order i and type 1.
22. Search DoE for xp2 anywhere in the DoE regardless of position in the sequences. If found, take the value of the corresponding displacement $d_i$ and go to 10. The displacement found is an occurrence of order i and type 2.
23. $D=D+d_i$.
24. if i=wp then STOP. The end of the sequence has been reached. In the example presented here, wp=6 which corresponds to 6 welding events per sequence.
25. i=i+1.
26. go to step 4.

This process is very much faster to compute than a run of the FE model. Thus, using the results of a relatively small number of FE runs to populate the DoE, the surrogate model can rapidly run through all the possible sequences and identify the smallest total displacement.

To illustrate the idea of using these occurrences, consider a model based on terms up to $R_2'$:

$$D = M_{w_i} + \sum_{i=2}^{6} (M_{w_i} + \Delta R_1'(v, i) + \Delta R_2'(v, i)), \qquad (5)$$

where $\Delta R_1'(v,i)=R_1'(v,i)-M_{w_i}$; $\Delta R_2'(v,i)=R_2'(v,i)-M_{w_i}$; i is the position in the sequence; and $v=[w_{i-k+1}, \ldots, w_{i-1}, w_i]$, where k=1 and 2, respectively.

Run 20 provides information about the following occurrences of second order: $R_2'(2, -5, 2)$; $R_2'(-5, 6, 3)$; $R_2'(6, -1, 4)$; $R_2'(-1, 3, 5)$; $R_2'(3, -4, 6)$, where the last number in each group is the position in the sequence of the two welding events represented by the first two numbers. 180 runs of the FE model are needed to fill the whole $R_2'$ DoE matrix, and this makes its use unattractive. Instead, it is possible to compromise by using a DoE that fills the whole $R_2''$ matrix instead. To ensure that all occurrences of second order and type two exist, 27 FE runs are required. It can be shown that this approximation, which ignores where the sub-sequence pairs have occurred, does not cause a great loss of accuracy. Moreover, some $R_2'$ pairs will be available from the matrix, and can be used if available. Therefore, the terms $R_2'$ in (5) can be replaced by $$\overline{R}_2(v, i) = \begin{cases} R_2'(v, i) & \text{if it exists in the } DoE \\ R_2''(v) & \text{if the above does not exist in the } DoE \\ 0 & \text{if neither of the above exists in the } DoE \end{cases} \quad (6)$$

Thus, the second order terms are used wherever possible, and only replaced by lower order terms if unavailable. This small loss in accuracy is balanced by the reduction in the number of FE runs needed for the DoE.

Although the DoE is designed to include all possible occurrences of $R_2''(v)$, for some events and positions it will contain occurrences of third order and higher, which may be used to improve the accuracy further. Thus, equation 6 can be generalised to:

$$H(i) = \begin{cases} \overline{R}_i & \text{if } \overline{R}_i \in DoE, \quad \text{else} \\ \overline{R}_{i-1} & \text{if } \overline{R}_{i-1} \in DoE, \quad \text{else} \\ \vdots \\ M_{w_i} & \text{if } M_{w_i} \in DoE, \quad \text{else} \\ M_w & \text{if } M_w \in DoE, \quad \text{else} \\ 0 \end{cases} \quad (7)$$

and the total displacement defined as $$D = \sum_{i=1}^{n} H(i) \quad (8)$$

where n is the total number of events in the sequence; n=6 in the present example. Equation 8 is a more general form of equation (5) that finds the sum of the combination of the highest occurrences of lowest type to calculate the predicted value for the displacement for a given welding event and sequence position.

This model can be applied to any number of variables or events n, bearing in mind that the highest order of occurrence is equal to the number of variables. The model exhibits some l earning properties, in the sense that it will always produce a prediction if there is at least one point in the DoE. If more FE runs are performed, the DoE grows in size, and the predictions will become more accurate. In the limit when all possible combinations have been tested by the FE model it reproduces the trial data exactly. This feature allows the surrogate model to be used with any number of points in the DoE, giving the freedom for the latter to grow or stop growing, according to the desired accuracy of the model. For the example studied here experience suggests that the existence of the complete $R_2''$ set is enough to ensure a good fit to the existing data.

It is clear that once displacement data has been calculated from sufficient FE runs as defined by the DoE, such a model requires very little computation, and this enables all possible combinations to be examined by the surrogate model and the best one selected. To test the accuracy, this best prediction can then be checked by running its weld sequence through the FE model. This FE run can then be added to the DoE, making further predictions of the surrogate model more accurate.

Another full search of the combination can then be performed by the surrogate model, using all the DoE information, including that from the latest FE run and so on, until successive models produce the same or sufficiently similar results.

Figure 10:
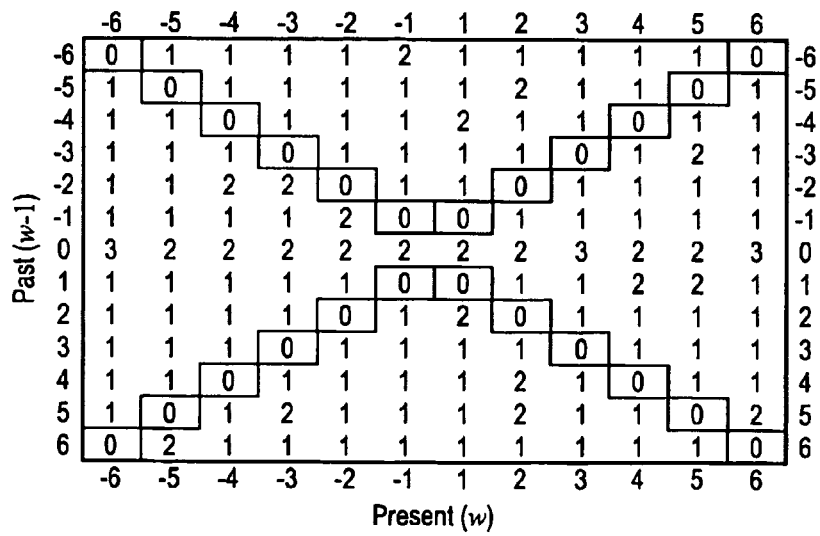
FIG. 10 shows a matrix of the occurrences of various combinations of welding paths found in the sequences of FIG. 9.

Continuing with the welding sequence optimisation as an illustration of an embodiment of the present invention, and following the conclusions reached above, FIG. 9 shows a table of a DoE corresponding to 27 runs of the FE model, that ensure that all $R_2''$ occurrences are included. FIG. 10 shows a matrix that indicates the number of occurrences of second order and type 2 for each combination of present and past welding positions found in the DoE shown in FIG. 9. The first element of this matrix (1, 1) is equal to 0, since welding event −6 cannot be performed after welding event −6; hence all diagonal elements are 0. The element below, (2, 1), is equal to 1, showing that there is one occurrence of the past-present event pair (−5, −6). It appears in run 2, appearing at the sixth position. The matrix row indexed 0 contains the main effects. One can see, for instance, that there are 3 runs giving information for the main effect −6. These occur in runs 6, 7 and 23, where welding event −6 has been executed first in the welding sequence. This matrix confirms that there are no zero elements except on the diagonal.

The DoE in this example was constructed by considering all possible 46080 combinations and selecting the first set that filled all non-diagonal elements in the matrix shown in FIG. 10. This was achieved by running six nested loops, each one running through the values −6, −5, −4, −3, −2, −1, 1, 2, 3, 4, 5, 6 and selecting the sequences that obey the following rule |A|≠|B|≠|C|≠|D|≠|E|≠|F| where A, B, C, D, E and F are the six nested loops variables. Each sequence is registered in the matrix, as shown in FIG. 10, and when all but diagonal elements are non-zero, the DoE generation stops. This produces a DoE that contains the first set of sequences that guarantees that all $R_2''$ occurrences are tested. This is a particularly simple way of generating the DoE, but it should be noted that the result is not necessarily the optimal DoE, nor the smallest possible DoE, although the smallest possible DoE is not expected to be much smaller in size than that shown here.

Each sequence in the DoE is run through the FE model. For each element of the matrix of FIG. 10, the value of displacement is calculated from the difference of the displacement at the end and beginning of a weld as calculated by the FE model. The results of this are shown in the table of FIG. 11, which has the same structure as the matrix of FIG. 10. For instance, the displacement caused by the occurrence of the past-present pair (−5, −6) is −0.12721 mm, and this is the value for $R_2''(-5, -6)$.

For illustration purposes, consider the welding sequence 6, 3, −5, 4, −2, 1, and apply the model to it:

8. D=0.
9. 1=1: For position number 1, the highest order of occurrence is 1 so check if there is a main effect for 6 in the DoE points. Three entries are found (in runs 8, 24, 25). The displacement for a main effect of 6 is extracted from FIG. 11. The value is added to D, and now D=$M_6$.
10. i=2: The highest order of occurrence is 2, so look for the pair (6, 3) within the DoE at position 2 (an occurrence of type 1 is sought first). There is no match, so next look for occurrences of type 2, regardless of position. A match is found in run 27. Add the corresponding value of displacement from FIG. 11 to the value of D, so that D=$M_6$+$R_2''$(6, 3).
11. i=3: The highest order of occurrence is 3, so look for the sub-sequence (6, 3, −5) within the DoE at position 3 (again, an occurrence of type 1 is sought first). This subset cannot be found in the DoE. A check for this triple anywhere in the DoE also fails, indicating that there is no such third order occurrence of either type 1 or type 2. Next, reduce the subset by truncating the farthest event, which presumably has least effect on the deflection generated at position 3. The subset becomes (3, −5). Again, check first for its occurrence of type 1, i.e., such that event −5 stands at position 3 and event 3 stands at position 2. A match is found in run 18, and the corresponding displacement is added to the value of D, so that D=$M_6$+$R_2''(6, 3)$+$R_2'(3, -5, 3)$.

12. i=4: The highest order of occurrence is 4, so look for the sub-sequence (6, 3, −5, 4) within the DoE at position 4, for an occurrence of type 1. There is no match, so look for occurrences of type 2, which cannot be found either. Next, truncate the subset to (3, −5, 4) and look first for occurrences of type 1. There is a match in run 18, so add the appropriate value of displacement contributed by the $R_3'$ term to the value of D, so that D=$M_6$+$R_2''(6, 3)$+$R_2'(3, -5, 3)$+$R_3'(3, -5, 4, 4)$.

13. i=5: The highest order of occurrence is 5, so look for the sub-sequence (6, 3, −5, 4, −2) within the DoE at position 5, for an occurrence of type 1. None is found, and neither is a type 2 occurrence, so truncate and look for (3, −5, 4, −2). The search again fails for both type 1 and type 2. Truncate further to (−5, 4, −2). Again no match is found for either type. Truncate to (4, −2). There is no type 1 occurrence, but a type 2 occurrence appears in run 4. Add the displacement to D, so that D=$M_6$+$R_2''(6, 3)$+$R_3'(3, -5, 3)$+$R_3'(3, -5, 4, 4)$+$R_2''(4, -2)$.

14. i=6: The highest order of occurrence is 6, so look for the sub-sequence (6, 3, −5, 4, −2, 1) within the DoE at position 6. Unsurprisingly it is not found. Go through the same procedure as in the previous stage, checking for occurrences of type 1 and 2, of the following subsets (3, −5, 4, −2, 1); (−5, 4, −2, 1); (4, −2, 1). None is found. Finally, a search for (−2, 1) anywhere in the DoE, regardless of position, finds a match in run 14. Add the displacement to D, so that D=$M_6$+$R_2''(6, 3)$+$R_2'(3, -5, 3)$+$R_3'(3, -5, 4, 4)$+$R_2''(4, -2)$+$R_2''(-2, 1)$.

8. The total displacement should also include the final cooling stage, which has been found using a linear curve fit to be modelled by $d^c$=0.7152*H(6)+0.0143.

Using the above algorithm, all 46080 possible combinations may be calculated in less than 5 minutes on 800 MHz Pentium DI machine, using a MATLAB code. A code written in C or FORTRAN would produce results much faster. It has been found that the following sequence, labelled 'Run 28', produces the least value for |D|: −6, −1, −5, 2, −4, 3. The value of the displacement for this sequence is given by:

$$D = M_{-6} + R'_2(-6, -1, 2) + R'_3(-6, -1, -5, 3) + R''_2(-5, 2, 4) +$$
$$R''_2(2, -4, 5) + R''_2(-4, 3, 6) + 0.7152*$$
$$R''_2(-4, 3, 6) + 0.0143$$
$$= 0.00023$$

The same sequence has been calculated using the FE model, and this produced a very similar result: D=0.000231. This is considered as a satisfactorily accurate value for the manufacture of TBHs, and is also the likely global minimum for this optimisation task.

Figure 12:
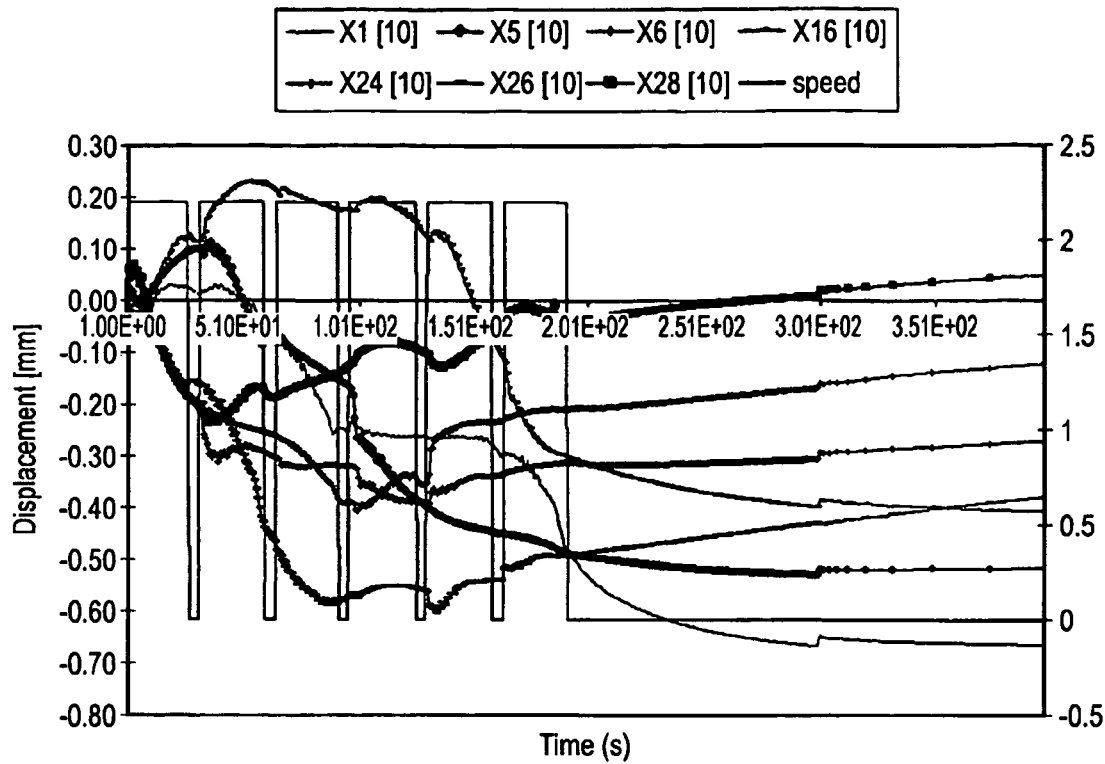
FIG. 12 shows graphs of the variation in displacement of a part of the vane during the welding process for some of the sequences of FIG. 9.

FIG. 12 shows a graph that illustrates the final optimisation result as plots of displacement against time, which shows the FE simulation of Run 28 together with the Runs 1, 5, 6, 16, 24 and 26 from the DoE for comparison purposes. The curve for Run 28 reaches zero just before second 300, when the clamps are released. The comparison illustrates the improvement of the X displacement in comparison to Run 1, which is a sequence commonly adopted as standard in TBH production.

Figure 13:
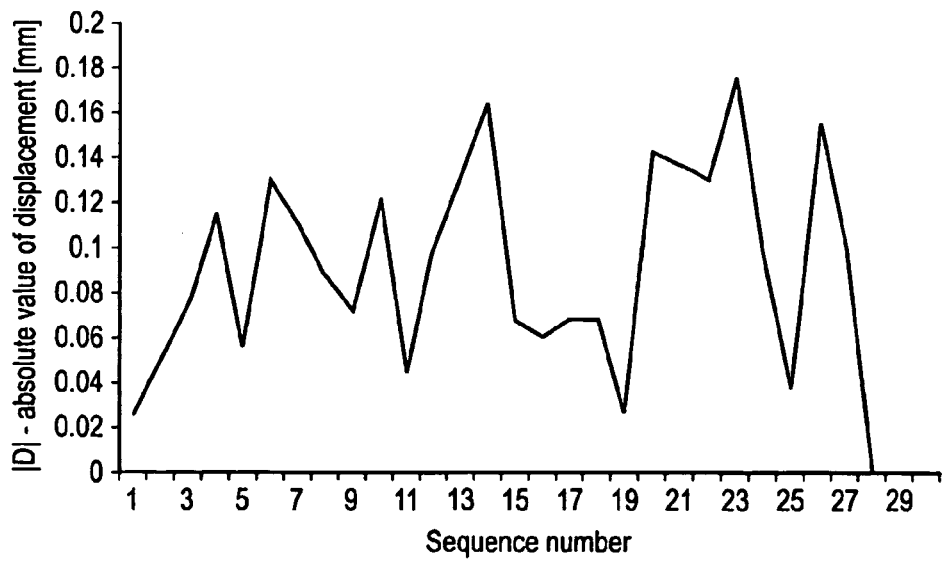
FIG. 13 shows a graph of the final displacement of a part of the vane for each sequence in FIG. 9.

FIG. 13 shows a graph of the final displacements for all 28 runs, which illustrates that the optimised Run 28 produces minimal displacement.

Thus, the present invention has been advantageously applied to the optimisation of a welding sequence, and has demonstrated that optimum post-weld distortions can be determined with only 28 runs of an FE model, out of a possible 46080 sequence combinations. This greatly reduces the computational expense needed in weld planning, without significant loss of accuracy.

A number of observations highlighting the advantages of the present invention may be made, many of which apply to application of the invention to other sequential combinatorial sequences:

- the method maps the non-continuous space of the sequential process to a continuous one, allowing the conversion of a sequential combinatorial problem to a conventional representation;
- the method is applicable to a wide variety of sequential combinatorial problems;
- the surrogate model is built up sequentially, so that every new combination presented to makes it more accurate;
- the surrogate model is efficient, in that it extracts all the useful information out of the presented master model runs, and arranges this in a priority list, based on its usefulness;
- the method is fast; for six events all possible 46080 combinations may be calculated by the surrogate model in less than 5 minutes on a 800 M Hz Pentium III machine, using a MATLAB code. A code written in C or FOR-TRAN would produce results much faster;
- in the context of the example of optimisation of the welding process described above, 27 initial master model calculations were sufficient to obtain a high accuracy, fast prediction from the surrogate model, which produced the following value for the optimal displacement: 0.00023 mm, which is very close to the FE predicted value of 0.000231 mm.

Further Embodiments

The present invention as described above provides a fast and effective substitute to computationally expensive FE and other models that are conventionally applied in sequential combinatorial problems. The algorithm continuously refers to existing information about the system of interest, by thus mapping a discrete non-numerical set of information to a continuous numerical domain. To allow it to function with low number of expensive runs from a full, master model, the surrogate model predicts following a priority list of matching conditions. An example of this is:

1. Occurrences of highest possible order of type 1
2. Occurrences of highest possible order of type 2
3. Occurrences of lower order of type 1
4. Occurrences of lower order of type 2
5. Main effects Embodiments of the proposed algorithm will always try to find an item placed as high as possible in this list. For some problems it might be more suitable to apply an alternative priority list, such as:

1. Occurrences of highest possible order of type 1
2. Occurrences of lower order of type 1

3. Occurrences of highest possible order of type 2
4. Occurrences of lower order of type 2
5. Main effects Other priority lists are also possible, and may be studied to improve predictions in a given system.

The algorithm will produce a zero result for all predictions if no runs from the master model are available. A very rough prediction, which may be adequate for some applications, can be obtained by ensuring that at least all the main effects are available. For systems that do not exhibit memory, such a prediction should be fairly accurate. Main effects can be obtained by running only the first events, without computing the whole sequence. This gives a very rapid optimisation process, since little intensive computation is required compared to full calculation of all possible sequences. However, if more accurate results are required, the inclusion of at least second order occurrences of type 2 is recommended.

For high dimensional problems, containing a large number of events, accuracy can be improved by giving higher priority to some positions or events than others. In such cases, a mixed DoE is possible, where the most important events are captured with higher order of occurrence and the less significant events with a lower order. Thus, the computational expense is concentrated on those parts of the sequence that have the greatest impact on the end result. Variations in this respect can lead to reduced size DoEs, giving most information for the more important events.

Although an embodiment of the invention has been described in detail with respect to the example of a welding sequence, it is not so limited. The invention is applicable to any sequential process in which the ordering of the sequence affects the outcome of the process. Examples of processes to which the invention may be applied include:

welding of a plurality of vanes to the rings of a gas turbine TBH or similar turbine or propeller structure, i.e. the sequence in which the vanes are welded to the rings; and
finding the optimum joining sequence with respect to mechanical properties of one or more arbitrary geometries that are joined by welding, glueing, bolt connections, shrink fitting, laminate bonding or any other joining process that is dependent on the order on which different work tasks are done.

Also, the invention is not limited to finite element analysis models as the master model. Any type of model capable to providing the desired information can be used. For example, the master model may be any suitable computer program capable of simulating a deflection or other operation parameter. However, a computer simulation model is not required. For instance the results of real tests, in which the process is performed for a selection of sequences, may be used in place of or in conjunction with simulated results.

For example, in the application of component flow through a factory, it may be possible to use a timer to measure time intervals for different machines/operations, and use these as the information used by the surrogate model.

Similarly, results from tests of similar or related processes might be suitable for use, perhaps by being modified to more closely model the process of interest. Also, the use of real results may be combined with a master model, so that the DoE may comprise some sequences that have been run through the master model and some sequences for which real results have been measured, and/or the master model may be used to check the accuracy of the surrogate model prediction. In effect, any values of the contributions to the end result for each event in a sequence, where the sequence is included in the design of experiments, may be used as the information referred to by the surrogate model, no matter how it has been obtained. Thus, the most convenient technique for obtaining the information can be used.

REFERENCES

[1] U.S. Pat. No. 6,349,467
[2] Winston, W, 1995, "Introduction to mathematical programming", second edition, Duxbury Press, California, USA.

The invention claimed is:

1. A method of optimising a manufacturing, industrial or engineering sequential combinatorial process comprising a plurality of interchangeable events performable in any of many sequences to achieve an end result of the process, the end result being defined by an operation parameter, wherein the method is implemented at least in part by a computer, and wherein said operation parameter for a particular sequence is dependent on how the interchangeable events for said sequence are ordered, the method comprising:

using a design of experiments comprising a plurality of sequences selected from the many sequences of interchangeable performable events, each sequence from the design of experiments being linked to information regarding values of contributions to the end result, in terms of the operation parameter, for each event in each sequence;
using a surrogate model of the process that takes as an input a sequence of the events and determines a value of the end result by summing values of contributions to the end result for each event in the input sequence, where the values of the contributions are selected from the values of the contributions from the operation parameter information according to an algorithm that searches the design of experiments for a match between each event of the input sequence and the events in the sequences of the design of experiments according to a priority list of matching conditions and retrieves the value of the contribution for the matched event;
running a plurality of the many sequences through the surrogate model and recording the value of the end result for each sequence; and
identifying an optimum sequence by searching the recorded values of the end result from the surrogate model to find a recorded optimum value of the operation parameter, the sequence that gives this recorded optimum value being the optimum sequence.

2. A method according to claim 1, and further comprising obtaining the information to which each sequence from the design of experiments is linked by running each sequence from the design of experiments through a master model of the process that takes as a input a sequence of the events and determines a value of the end result and values of contributions to the end result of each event in the input sequence.

3. A method according to claim 2, and further comprising constructing the master model before running each sequence from the design of experiments through the said master model.

4. A method according to claim 2, in which the surrogate model is a simplified approximation of the master model.

5. A method according to claim 2, and further comprising:
after identifying the optimum sequence, running the identified optimum sequence through the master model to determine a value of the end result, and comparing the recorded optimum value for the identified optimum sequence determined by the surrogate model with the end result determined by the master model to check accuracy of the identification of the optimum sequence.

6. A method according to claim 5, and further comprising: if the recorded optimum value for the identified optimum sequence determined by the surrogate model and the end result determined by the master model are found to differ by more than a predetermined amount for the process, adding the identified optimum sequence to the design of experiments so that this sequence and values of contributions to the end result for each event as determined by the running of the identified optimum sequence through the master model are available for searching and retrieval by the surrogate model algorithm;

running a plurality of the many sequences through the surrogate model to determine new values of the end result for each sequence; and identifying a new optimum sequence from the new end results.

7. A method according to claim 6, and further comprising repeating for the new identified optimum sequence the steps of running the new identified optimum sequence through the master model to determine a value of the end result; comparing the recorded optimum value for the identified optimum sequence determined by the surrogate model with the end result determined by the master model to check accuracy of the identification of the optimum sequence; if the recorded optimum value for the identified optimum sequence determined by the surrogate model and the end result determined by the master model are found to differ by more than a predetermined amount for the process, adding the identified optimum sequence to the design of experiments so that this sequence and values of contributions to the end result for each event as determined by the running of the identified optimum sequence through the master model are available for searching and retrieval by the surrogate model algorithm; running a plurality of the many sequences through the surrogate model to determine new values of the end result for each sequence; and identifying a new optimum sequence from the new end results, until the recorded optimum value for the identified optimum sequence determined by the surrogate model and the end result determined by the master model differ by less than a predetermined amount for the process.

8. A method according to claim 1, and further comprising obtaining the information to which each sequence from the design of experiments is linked by performing the sequential combinatorial process using each of the sequences in the design of experiments, and recording the values of contributions to the end result for each event in each sequence.

9. A method according to claim 1, and further comprising constructing the surrogate model before running the plurality of the many sequences through the said surrogate model.

10. A method according to claim 1, in which the priority list comprises a hierarchy of matching conditions requiring a decreasing level of matching between an event in the sequence input to the surrogate model and events in the sequences of the design of experiments in terms of position of the event within the input sequence and/or events preceding the event in the input sequence.

11. A method according to claim 1, in which the matching conditions are defined so as to have:

an order that specifies a number of events preceding an event in the sequence input to the surrogate model that are required to be matched with events preceding an event in the sequences of the design of experiments; and a type that specifies whether or not a position of an event in the sequence input to the surrogate model within that sequence matches a position of an event within the sequences of the design of experiments, such that a type 1 match requires that the position of an event in the input sequence matches the position of an event within the sequences of the design of experiments, and a type 2 match does not require that the position of an event in the input sequence matches the position of an event within the sequences of the design of experiments.

12. A method according to claim 11, in which for a sequence comprising n events, the priority list comprises the following matching conditions:

a match of order n of type 1;
a match of order n of type 2;
a match of order n−1 of type 1;
a match of order n−1 of type 2

. . .

a match of order 1 of type 1;
a match of order 1 of type 2;
a match of an event at any position in the sequence with the same event occurring in a first position of any sequence in the design of experiments.

13. A method according to claim 11, in which for a sequence comprising n events, the priority list comprises the following matching conditions:

a match of order n of type 1;
a match of order n−1 of type 1;
a match of order of n−2 of type 1;

. . .

a match of order 1 of type 1;
a match of order n of type 2;
a match of order n−1 of type 2;
a match of order n−2 of type 2;

. . .

a match of order 1 of type 2;
a match of an event at any position in the sequence with the same event occurring in a first position of any sequence in the design of experiments.

14. A method according to claim 11, in which the design of experiments comprises a selection of sequences from the many sequences that contain events which provide matches with at least all combinations of events of a selected order and type of matching condition.

15. A method according to claim 1, in which the design of experiments comprises a random selection of sequences from the many sequences.

16. A method according to claim 1, and further comprising determining the design of experiments.

17. A method according to claim 1, in which running a plurality of the many sequences through the surrogate model comprises running all of the many sequences through the surrogate model.

18. A method according to claim 1, and further comprising carrying out the sequential combinatorial process using the identified optimum sequence of events.

19. A method according to claim 1, in which the sequential combinatorial process comprises welding a vane to a ring of a gas turbine tail bearing housing, the events being individual welding paths arranged in a sequence, the operation parameter defining the end result being a distortion of a tip portion of the vane, and the optimum value of the operation parameter being a minimum value of the distortion.

20. A method according to claim 1, in which the sequential combinatorial process comprises machining a component from a workpiece, the events being cutting steps arranged in a sequence, the operation parameter defining the end result being a shape of the component, and the optimum value of the operation parameter being a desired shape of the component.

21. A method according to claim 1, in which the sequential combinatorial process comprises machining a component from a workpiece, the events being cutting steps arranged in a sequence, the operation parameter defining the end result being a quality of the component, and the optimum value of the operation parameter being a best value of the quality of the component.

22. A method according to claim 1, in which the sequential combinatorial process comprises machining a component from a workpiece, the events being cutting steps arranged in a sequence, the operation parameter defining the end result being vibration of the component during machining arising from insufficient structural stiffness, and the optimum value of the operation parameter being a minimum amount of vibration.

23. A method according to claim 1, in which the sequential combinatorial process comprises heat treatment of a component, the events being individual heating and/or cooling steps arranged in a sequence, the operation parameter defining the end result being a shape, stiffness or material microstructure of the component, and the optimum value of the operation parameter being a desired shaped, stiffness or material microstructure.

24. A method according to claim 1, in which the sequential combinatorial process comprises shaping a component, the events being individual shaping steps arranged in a sequence, the operation parameter defining the end result being a shape, stiffness or material microstructure of the component, and the optimum value of the operation parameter being a desired shape, stiffness or material microstructure.

25. A method according to claim 1, in which the sequential combinatorial process comprises manufacturing a component, the events being individual steps of machining, cutting, shaping and/or heat treating arranged in a sequence, the operation parameter defining the end result being a shape, stiffness or material microstructure of the component, and the optimum value of the operation parameter being a desired shape, stiffness or material microstructure.

26. A method according to claim 1, in which the sequential combinatorial process comprises the flow of material and/or components in a factory, the events being individual steps of transportation of the material and/or components between sites in the factory arranged in a sequence, the operation parameter defining the end result being a duration of the sequence, and the optimum value of the operation parameter being a minimum value of the duration.

27. A method according to claim 1, in which the sequential combinatorial process comprises the flow of material and/or components in a factory, the events being individual steps of transportation of the material and/or components between sites in the factory arranged in a sequence, the operation parameter defining the end result being a rate of the flow, and the optimum value of the operation parameter being a maximum value of the rate of flow.

28. A method according to claim 1, in which the sequential combinatorial process comprises pumping oil or gas through a pipeline network, the events being individual portions of the network defined by pipeline having associated pipeline components, pumping rates and valve operation arranged in a sequence, the operation parameter defining the end result being a delivery pattern of the oil or gas, and the optimum value of the operation parameter being a desired delivery pattern.

29. A method according to claim 1, in which the sequential combinatorial process comprises the mixing of components or ingredients, the events being steps of adding various components or ingredients to a mixture, the steps arranged in a sequence, the operation parameter defining the end result being a quality of the mixture such as stability, purity or homogeneity, and the optimum value of the operation parameter being a desired quality.

30. A method according to claim 1, in which the sequential combinatorial process comprises a numerical method describing the behaviour of biological components, the events being individual interaction steps between components arranged in a sequence, the operation parameter defining the end result being an end result of a sequence, and the optimum value of the operation parameter being a known end result.

31. A method according to claim 1, in which the sequential combinatorial process comprises a "knapsack" problem, the events being individual items to be loaded into the knapsack in a sequence, the operation parameter defining the end result being a value of items in the knapsack, and the optimum value of the operation parameter being a maximum value.

32. A method according to claim 1, in which the sequential combinatorial process comprises linking transportation units in a chain, the events being individual units linked in a sequence, the operation parameter defining the end result being a time taken to disassemble and reassemble the chain to remove and/or add units, and the optimum value of the operation parameter being a minimum amount of time.

33. A computer program product comprising a computer-readable storage medium on which are stored machine-readable instructions for implementing a method of optimising a manufacturing, industrial or engineering sequential combinatorial process comprising a plurality of interchangeable events performable in any of many sequences to achieve an end result of the process, the end result being defined by an operation parameter, wherein said operation parameter for a particular sequence is dependent on how the interchangeable events for said sequence are ordered, the instructions operable to instruct a machine to:
  store a design of experiments comprising a plurality of sequences selected from the many sequences of interchangeable performable events;
  store information linked to each sequence from the design of experiments, the information regarding values of contributions to the end result, in terms of the operation parameter, of each event in each sequence from the design of experiments;
  run a plurality of the many sequences through a surrogate model of the process that takes as an input a sequence of the events and determines a value of the end result by summing values of contributions to the end result for each event in the input sequence, where the values of the contributions are selected from the values of the contributions from the operation parameter information according to an algorithm that searches the design of experiments for a match between each event of the input sequence and the events in the sequences of the design of experiments according to a priority list of matching conditions and retrieves the value of the contribution for the matched event, and record the value of the end result for each sequence; and
  identify an optimum sequence by searching the recorded values of the end result from the surrogate model to find a recorded optimum value of the operation parameter, the sequence that gives this recorded optimum value being the optimum sequence.

34. A computer program product according to claim 33, in which the instructions are further operable to instruct a machine to calculate the information linked to each sequence from the design of experiments by running each sequence from the design of experiments through a master model of the process that takes as an input a sequence of the events and determines a value of the end result and values of contributions to the end result of each event in the input sequence.

35. A computer program product according to claim 34, in which the surrogate model is a simplified approximation of the master model.

36. A computer program product according to claim 34, in which the instructions are further operable to instruct a machine to:
after identifying the optimum sequence, to run the identified optimum sequence through the master model to determine a value of the end result, and compare the recorded optimum value for the identified optimum sequence determined by the surrogate model and the end result determined by the master model to check accuracy of the identification of the optimum sequence.

37. A computer program product according to claim 36, in which the instructions are further operable to instruct a machine to:
if the recorded optimum value for the identified optimum sequence determined by the surrogate model and the end result determined by the master model are found to differ by more than a predetermined amount for the process, to add the identified optimum sequence to the design of experiments so that this sequence and values of contributions to the end result for each event as determined by the running of the identified optimum sequence through the master model are available for searching and retrieval by the surrogate model algorithm;
run a plurality of the many sequences through the surrogate model to determine new values of the end result for each sequence; and
identify a new optimum sequence from the new end results.

38. A computer program product according to claim 37, in which the instructions are further operable to instruct a machine to repeat for the new identified optimum sequence the steps of running the new identified optimum sequence through the master model to determine a value of the end result; comparing the recorded optimum value for the identified optimum sequence determined by the surrogate model with the end result determined by the master model to check accuracy of the identification of the optimum sequence; if the recorded optimum value for the identified optimum sequence determined by the surrogate model and the end result determined by the master model are found to differ by more than a predetermined amount for the process, adding the identified optimum sequence to the design of experiments so that this sequence and values of contributions to the end result for each event as determined by the running of the identified optimum sequence through the master model are available for searching and retrieval by the surrogate model algorithm; running a plurality of the many sequences through the surrogate model to determine new values of the end result for each sequence; and identifying a new optimum sequence from the new end results, until the recorded optimum value for the identified optimum sequence determined by the surrogate model and the end result determined by the master model differ by less than a predetermined amount for the process.

39. A computer program product according to claim 33, in which the information linked to each sequence from the design of experiments comprises values of contributions to the end result of each event in each sequence of the design of experiments obtained from performing the sequential combinatorial process using each of the sequences in the design of experiments.

40. A computer program product according to claim 33, in which the priority list comprises a hierarchy of matching conditions requiring a decreasing level of matching between an event in the sequence input to the surrogate model and events in the sequences of the design of experiments in terms of position of the event within the input sequence and/or events preceding the event in the input sequence.

41. A computer program product according to claim 33, in which the matching conditions are defined so as to have:
an order that specifies a number of events preceding an event in the sequence input to the surrogate model that are required to be matched with events preceding an event in the sequences of the design of experiments; and
a type that specifies whether or not a position of an event in the sequence input to the surrogate model within that sequence matches a position of an event within the sequences of the design of experiments, such that a type 1 match requires that the position of an event in the input sequence matches the position of an event within the sequences of the design of experiments, and a type 2 match does not require that the position of an event in the input sequence matches the position of an event within the sequences of the design of experiments.

42. A computer program product according to claim 41, in which for a sequence comprising n events, the priority list comprises the following matching conditions:
a match of order n of type 1;
a match of order n of type 2;
a match of order n−1 of type 1;
a match of order n−1 of type 2
. . .
a match of order 1 of type 1;
a match of order 1 of type 2;
a match of an event at any position in the sequence with the same event occurring in a first position of any sequence in the design of experiments.

43. A computer program product according to claim 41, in which for a sequence comprising n events, the priority list comprises the following matching conditions:
a match of order n of type 1;
a match of order n−1 of type 1;
a match of order of n−2 of type 1;
. . .
a match of order 1 of type 1;
a match of order n of type 2;
a match of order n−1 of type 2;
a match of order n−2 of type 2;
. . .
a match of order 1 of type 2;
a match of an event at any position in the sequence with the same event occurring in a first position of any sequence in the design of experiments.

44. A computer program product according to claim 41, in which the design of experiments comprises a selection of sequences from the many sequences that contain events which provide matches with at least all combinations of events of a selected order and type of matching condition.

45. A computer program product according to claim 33, in the design of experiments comprises a random selection of sequences from the many sequences.

46. A computer program product according to claim 33, in which the instructions are further operable to instruct a machine to select sequences for the design of experiments.

47. A computer program product according to claim 33, in which the instructions are operable to instruct a machine to run all of the many sequences through the surrogate model.

48. A computer program product according to claim 33, in which the sequential combinatorial process comprises welding a vane to a ring of a gas turbine tail bearing housing, the events being individual welding paths arranged in a sequence, and operation parameter defining the end result being a distortion of a tip portion of the vane, and the optimum value of the operation parameter being a minimum value of the distortion.

49. A computer system for implementing a method of optimising a manufacturing, industrial or engineering sequential combinatorial process comprising a plurality of interchangeable events performable in any of many sequences to achieve an end result of the process, the end result being defined by an operation parameter, wherein said operation parameter for a particular sequence is dependent on how the interchangeable events for said sequence are ordered, the computer system comprising:

memory for storing a design of experiments comprising a plurality of sequences selected from the many sequences of interchangeable performable events, and information linked to each sequence from the design of experiments, the information regarding values of contributions to the end result, in terms of the operation parameter, of each event in each sequence from the design of experiments; and a processor programmed to:

run a plurality of the many sequences through a surrogate model of the process that takes as an input a sequence of the events and determines a value of the end result by summing values of contributions to the end result for each event in the input sequence, where the values of the contributions are selected from the values of the contributions from the operation parameter information according to an algorithm that searches the design of experiments for a match between each event of the input sequence and the events in the sequences of the design of experiments according to a priority list of matching conditions and retrieves the value of the contribution for the matched event, and record the value of the end result for each sequence in the memory; and identify an optimum sequence by searching the recorded values of the end result from the surrogate model to find a recorded optimum value of the operation parameter the sequence that gives this recorded optimum value being the optimum sequence.

50. A computer system according to claim 49, in which the processor is further programmed to calculate the information linked to each sequence from the design of experiments by running each sequence from the design of experiments through a master model of the process that takes as an input a sequence of the events and determines a value of the end result and values of contributions to the end result of each event in the input sequence.

51. A computer system according to claim 50, in which the surrogate model is a simplified approximation of the master model.

52. A computer system according to claim 50, in which the processor is further programmed to:

after identifying the optimum sequence, to run the identified optimum sequence through the master model to determine a value of the end result, and compare the recorded optimum value for the identified optimum sequence determined by the surrogate model and the end result determined by the master model to check accuracy of the identification of the optimum sequence.

53. A computer system according to claim 52, in which the processor is further programmed to:

if the recorded optimum value for the identified optimum sequence determined by the surrogate model and the end result determined by the master model are found to differ by more than a predetermined amount for the process, to add the identified optimum sequence to the design of experiments so that this sequence and values of contributions to the end result for each event as determined by the running of the identified optimum sequence through the master model are available for searching and retrieval by the surrogate model algorithm;

run a plurality of the many sequences through the surrogate model to determine new values of the end result for each sequence; and identify a new optimum sequence from the new end results.

54. A computer system according to claim 53, in which the processor is further programmed to repeat for the new identified optimum sequence the steps of running the new identified optimum sequence through the master model to determine a value of the end result; comparing the recorded optimum value for the identified optimum sequence determined by the surrogate model with the end result determined by the master model to check accuracy of the identification of the optimum sequence; if the recorded optimum value for the identified optimum sequence determined by the surrogate model and the end result determined by the master model are found to differ by more than a predetermined amount for the process, adding the identified optimum sequence to the design of experiments so that this sequence and values of contributions to the end result for each event as determined by the running of the identified optimum sequence through the master model are available for searching and retrieval by the surrogate model algorithm; running a plurality of the many sequences through the surrogate model to determine new values of the end result for each sequence; and identifying a new optimum sequence from the new end results, until the recorded optimum value for the identified optimum sequence determined by the surrogate model and the end result determined by the master model differ by less than a predetermined amount for the process.

55. A computer system according to claim 49, in which the information linked to each sequence from the design of experiments comprises values of contributions to the end result of each event in each sequence of the design of experiments obtained from performing the sequential combinatorial process using each of the sequences in the design of experiments.

56. A computer system according to claim 49, in which the priority list comprises a hierarchy of matching conditions requiring a decreasing level of matching between an event in the sequence input to the surrogate model and events in the sequences of the design of experiments in terms of position of the event within the input sequence and/or events preceding the event in the input sequence.

57. A computer system according to claim 49, in which the matching conditions are defined so as to have:

an order that specifies a number of events preceding an event in the sequence input to the surrogate model that are required to be matched with events preceding an event in the sequences of the design of experiments; and a type that specifies whether or not a position of an event in the sequence input to the surrogate model within that sequence matches a position of an event within the sequences of the design of experiments, such that a type 1 match requires that the position of an event in the input sequence matches the position of an event within the sequences of the design of experiments, and a type 2 match does not require that the position of an event in the input sequence matches the position of an event within the sequences of the design of experiments.

58. A computer system according to claim 57, in which for a sequence comprising n events, the priority list comprises the following matching conditions:
a match of order n of type 1;
a match of order n of type 2;
a match of order n−1 of type 1;
a match of order n−1 of type 2
. . .
a match of order 1 of type 1;
a match of order 1 of type 2;
a match of an event at any position in the sequence with the same event occurring in a first position of any sequence in the design of experiments.

59. A computer system according to claim 57, in which for a sequence comprising n events, the priority list comprises the following matching conditions:
a match of order n of type 1;
a match of order n−1 of type 1;
a match of order of n−2 of type 1;
. . .
a match of order 1 of type 1;
a match of order n of type 2;
a match of order n−1 of type 2;
a match of order n−2 of type 2;
. . .
a match of order 1 of type 2;
a match of an event at any position in the sequence with the same event occurring in a first position of any sequence in the design of experiments.

60. A computer system according to claim 57, in which the design of experiments comprises a selection of sequences from the many sequences that contain events which provide matches with at least all combinations of events of a selected order and type of matching condition.

61. A computer system according to claim 49, in the design of experiments comprises a random selection of sequences from the many sequences.

62. A computer system according to claim 49, in which the processor is further programmed to select sequences for the design of experiments.

63. A computer system according to claim 49, in which the processor is further programmed to run all of the many sequences through the surrogate model.

64. A computer system according to claim 49, in which the sequential combinatorial process comprises welding a vane to a ring of a gas turbine tail bearing housing, the events being individual welding paths arranged in a sequence, the operation parameter defining the end result being a distortion of a tip portion of the vane, and the optimum value of the operation parameter being a minimum value of the distortion.

* * * * *